United States Patent
Ruegg et al.

(10) Patent No.: US 12,257,293 B2
(45) Date of Patent: Mar. 25, 2025

(54) METHODS OF TREATMENT FOR CERVICAL DYSTONIA

(71) Applicant: REVANCE THERAPEUTICS, INC., Newark, CA (US)

(72) Inventors: Curtis L. Ruegg, Redwood City, CA (US); Jacob M. Waugh, Palo Alto, CA (US)

(73) Assignee: REVANCE THERAPEUTICS, INC., Newark, CA (US)

( * ) Notice: Subject to any disclaimer, the term of this patent is extended or adjusted under 35 U.S.C. 154(b) by 371 days.

(21) Appl. No.: 17/547,211

(22) Filed: Dec. 9, 2021

(65) Prior Publication Data

US 2022/0096610 A1 Mar. 31, 2022

Related U.S. Application Data

(63) Continuation of application No. 16/614,773, filed as application No. PCT/US2018/033397 on May 18, 2018, now abandoned.

(60) Provisional application No. 62/508,324, filed on May 18, 2017.

(51) Int. Cl.
| | | |
|---|---|---|
| A61K 38/48 | (2006.01) | |
| A61K 9/00 | (2006.01) | |
| A61K 47/26 | (2006.01) | |
| A61K 47/42 | (2017.01) | |
| A61P 21/00 | (2006.01) | |

(52) U.S. Cl.
CPC .......... *A61K 38/4893* (2013.01); *A61K 47/26* (2013.01); *A61K 47/42* (2013.01); *A61P 21/00* (2018.01); *A61K 9/0019* (2013.01)

(58) Field of Classification Search
CPC ................. A61K 38/4893; A61K 8/64; A61K 2800/592; A61K 2800/91; A61Q 19/08
See application file for complete search history.

(56) References Cited

U.S. PATENT DOCUMENTS

| | | | | |
|---|---|---|---|---|
| 7,211,261 | B1 * | 5/2007 | Moyer | A61P 1/02 424/234.1 |
| 8,557,256 | B2 | 10/2013 | Aoki et al. | |
| 2010/0168023 | A1 * | 7/2010 | Ruegg | A61P 21/02 514/8.9 |
| 2018/0311333 | A1 | 11/2018 | Ruegg et al. | |
| 2019/0290740 | A1 * | 9/2019 | Thompson | A61K 8/60 |
| 2020/0384090 | A1 | 12/2020 | Rubio | |

FOREIGN PATENT DOCUMENTS

| | | |
|---|---|---|
| EP | 2985039 A1 | 2/2016 |
| JP | 2012514003 A | 6/2012 |
| RU | 2741221 C1 | 1/2021 |
| WO | 2010078242 A1 | 7/2012 |
| WO | 2012094163 A1 | 7/2012 |
| WO | 2017075468 A1 | 5/2017 |
| WO | 2019090257 A1 | 5/2019 |
| WO | 2019113133 A1 | 6/2019 |

OTHER PUBLICATIONS

Marchetti et al., Movement Disorders, 2005; 20(8): 937-944 (Year: 2005).*
Brain Foundation, https://brainfoundation.org.au/disorders/cervical-dystonia/#:~:text=The%20muscles%20most%20commonly%20involved,sternocleidomastoideon%20the%20opposite%20side.&text=This%20is%20the%20second%20most%20common%20cervical%20dystonia; accessed on May 19, 2021 (Year: 2021).*
Camagro et al., Pain Relief in Cervical Dystonia with Botulinum Toxin Treatment, Toxins 2015, 7, 2321-2335.
Alvisi, "Botunlinum Toxin A Modifies Nociceptive Withdrawal Reflex in Subacute Stroke Patients," Brain and Behavior, Web. Jun. 19, 2018, pp. 1-10.
Author Unknown, "What is Cervical Dystonia?" Cervical Dystonia—Brain Disorders A-Z, Brain Foundation Australia, Web. https://brainfoundation.org.au/disorders/cervical-dystonia, accessed Jun. 14, 2022.
Thomas, Shane, International Search Report and Written Opinion from International Application No. PCT/US2022/017170, Jun. 7, 2022, pp. 1-10.
Young, Lee W, International Search Report and Written Opinion from International Application No. PCT/US2018/033397, Oct. 15, 2018, pp. 1-10.
Author Unknown, European Search Report and Search Opinion from corresponding application EP 18802488.9, Feb. 24, 2021, pp. 1-14.
Author Unknown, DazibotulinumtoxinA for Injection ASPEN, document summarizing Applicant's Phase 3 clinical trial results, pp. 1-5.
Author Unknown, Botox® FDA Label, Aug. 2011, pp. 1-31.
Author Unknown, Dysport® FDA Label, 2009, pp. 1-29.
Author Unknown, Xeomin® Product Website, WEB https://www.xeomin.com/healthcare-professionals/indications/cervical-dystonia, accessed Jun. 15, 2022.
Author Unknown, Myobloc®, Product Insert, Aug. 2019, pp. 1-20.
Jankovic, Joseph, Treatment of Cervical Dystonia With Botulinum Toxin, Movement Disorders, vol. 19, Suppl. 8, 2004, pp. S109-S115.

* cited by examiner

*Primary Examiner* — Brian Gangle
*Assistant Examiner* — Lakia J Jackson-Tongue
(74) *Attorney, Agent, or Firm* — Ballard Spahr LLP

(57) ABSTRACT

This invention provides methods to treat or prevent cervical dystonia, a disorder related thereto, or a symptom thereof, with novel injectable compositions comprising botulinum toxin that may be administered to a subject suffering from such maledy. The injectable compositions and methods in which these compositions are used provide novel and advantageous treatments which result in high responder rates and long duration of effect, for example, a duration of effect for 24 weeks and longer.

9 Claims, 8 Drawing Sheets

Specification includes a Sequence Listing.

| | Cohort 1 (N=12) | Cohort 2 (N=12) | Cohort 3 (n=13) | All (n=37) |
|---|---|---|---|---|
| Mean age (range) | 57 (46-74) | 52 (32-70) | 58 (30-69) | 56 (30-74) |
| Females, n (%) | 11 (92%) | 8 (67%) | 9 (69%) | 28 (76%) |
| Mean RT002 dose, U, (range) | 174 (100 to 200) | 229 (200 to 300) | 323 (300 to 450) | 244 (100 to 450) |
| Mean CD Disease Duration, years, (range) Median | 8.5 (0.4-21.7) 7.5 | 5.1 (0.02-24.1) 1.2 | 9.0 (0.6-23.3) 8.1 | 7.6 (0.02-24.1) 4.9 |
| Mean Baseline TWSTRS-Total Score | 43.8 | 44.9 | 43.7 | 44.1 |
| Prior Treatment with BotulinumtoxinA | 5 (42%) | 4 (33%) | 8 (62%)* | 17 (46%) |

*Three subjects received RT002 in Cohort 1 or 2, and re-enrolled to Cohort 3.

FIG. 2

|  | Cohort 1 (N=12) | Cohort 2 (N=12) | Cohort 3 (n=13) | All (n=37) |
|---|---|---|---|---|
| Number of treatment-related AEs | 8 | 8 | 6 | 22 |
| Subjects with any treatment-related A.E. n (%)* | 6 (50%) | 5 (42%) | 2 (15%) | 13 (35%) |
| Dysphagia | 1 (8%) | 2 (17%) | 2 (15%) | 5 (14%)** |
| Injection site erythema | 2 (17%) | 0 | 1 (8%) | 3 (8%) |
| Injection site bruising | 2 (17%) | 0 | 0 | 2 (5%) |
| Muscular weakness | 2 (17%)† | 0 | 0 | 2 (5%)† |
| Injection site pain | 0 | 1 (8%) | 1 (8%) | 2 (5%) |
| Muscle tightness | 0 | 1 (8%) | 0 | 2 (5%) |
| Neck pain | 1 (8%)‡ | 0 | 0 | 1 (3%)‡ |
| Fatigue | 0 | 1 (8%) | 0 | 1 (3%) |
| Muscle spasms | 0 | 1 (8%) | 0 | 1 (3%) |
| Nausea | 0 | 1 (8%) | 0 | 1 (3%) |
| Trismus | 0 | 0 | 0 | 1 (3%) |
| Asthenia | 0 | 0 | 1 (8%) | 1 (3%) |

\* Multiple events in a subject counted only once; \*\* All cases of dysphagia were mild in severity
† Muscle weakness included a mild (cervical paraspinal) and a moderate (cervical extensor) case
‡ A severe neck pain occurred at Day 10 and lasted for 2 days (200U)

FIG. 3

SEQUENCE LISTING

<160> NUMBER OF SEQ ID NOS: 10

<210> SEQ ID NO 1
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (32)..(51)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 1

Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
                20                  25                  30

Gly Gly Gly Gly Gly Gly Gly Gly Gly Gly Gly Gly Gly Gly Gly
            35                  40                  45

Gly Gly Gly
    50

<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (32)..(51)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 2

Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
                20                  25                  30

Gly Gly Gly Gly Gly Gly Gly Gly Gly Gly Gly Gly Gly Gly Gly
            35                  40                  45

Gly Gly Gly
    50

<210> SEQ ID NO 3
<211> LENGTH: 49
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (30)..(49)
<223> OTHER INFORMATION: This region may encompass 0-20 'Gly' residues
      wherein some positions may be absent
<220> FEATURE:
<223> OTHER INFORMATION: See specification as filed for detailed
      description of substitutions and preferred embodiments

<400> SEQUENCE: 3

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly Gly
            20                  25                  30

Gly Gly Gly Gly Gly Gly Gly Gly Gly Gly Gly Gly Gly Gly Gly
        35                  40                  45

Gly

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Lys Lys Arg Arg Gln Arg Arg Arg Gly Lys Lys Lys Lys Lys Lys
1               5                   10                  15

Lys Lys Lys Lys Lys Lys Lys Lys Lys Gly Arg Lys Lys Arg Arg Gln
            20                  25                  30

Arg Arg Arg
        35

<210> SEQ ID NO 5
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(20)
<223> OTHER INFORMATION: This region may encompass 0-20 'Gly' residues
      wherein some positions may be absent
<220> FEATURE:
<221> NAME/KEY: MISC_FEATURE
<222> LOCATION: (21)..(45)
<223> OTHER INFORMATION: This region may encompass 5, 7, 9, 11, 13, 15,
      17, 21, 23 or 25 'Arg' residues wherein some positions may be
      absent
<220> FEATURE:
<223> OTHER INFORMATION: See specification as filed for detailed
      description of substitutions and preferred embodiments

<400> SEQUENCE: 5

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg
```

```
                20                  25                  30
Arg Arg Arg Arg Arg Arg Arg Arg Arg Arg Arg
        35                  40                  45

<210> SEQ ID NO 6
<211> LENGTH: 19
<212> TYPE: PRT
<213> ORGANISM: Drosophila sp.

<400> SEQUENCE: 6

Ser Gly Arg Gln Ile Lys Ile Trp Phe Gln Asn Arg Arg Met Lys Trp
1               5                  10                  15

Lys Lys Cys

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Tyr Gly Arg Lys Lys Arg Arg Gln Arg Arg Gly Lys Lys Lys Lys
1               5                  10                  15

Lys Lys Lys Lys Lys Lys Lys Lys Lys Gly Tyr Gly Arg Lys
            20                  25                  30

Lys Arg Arg Gln Arg Arg Arg
        35

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Gly Arg Asp Asp Arg Arg Gln Arg Arg Gly Lys Lys Lys Lys
1               5                  10                  15

Lys Lys Lys Lys Lys Lys Lys Lys Lys Lys Gly Arg Gly Arg Asp
            20                  25                  30

Asp Arg Arg Gln Arg Arg Arg
        35

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 10-20 'Lys'
      residues wherein some positions may be absent
<220> FEATURE:
<223> OTHER INFORMATION: See specification as filed for detailed
      description of substitutions and preferred embodiments

<400> SEQUENCE: 9

Lys Lys Lys Lys Lys Lys Lys Lys Lys Lys Lys Lys Lys Lys Lys
1               5                  10                  15
```

```
Lys Lys Lys Lys
            20

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Arg Arg Arg Arg Arg Arg
1               5                   10
```

METHODS OF TREATMENT FOR CERVICAL DYSTONIA

SEQUENCE LISTING

The instant application contains a Sequence Listing which has been submitted electronically in ASCII format and is hereby incorporated by reference in its entirety. Said ASCII copy, created on Dec. 13, 2016, is named CD.txt and is 6,809 bytes in size.

FIELD OF THE INVENTION

This invention relates to methods to treat or prevent cervical dystonia, a disorder related thereto, or a symptom thereof, with novel injectable compositions comprising botulinum toxin that may be administered to a subject suffering from such malady. The injectable compositions and methods in which these compositions are used provide novel and advantageous treatments which result in high responder rates and long duration of effect, for example, a duration of effect for over 24 weeks.

BACKGROUND OF THE INVENTION

Cervical Dystonia is an extremely painful, chronic neurological movement disorder where the neck and shoulder muscles contract involuntarily and contort, causing abnormal movements and awkward posture of the head and neck such as the head to twist or turn to the left or right (torticollis), upwards (retrocollis), downwards (antecollis) or sideways (laterocollis). The movements may be sustained (tonic), jerky (clonic), or a combination. Cervical dystonia (also referred to as Neck Dystonia or Spasmodic Torticollis) affects a person's ability to control muscle activity. Cervical dystonia may be primary (meaning that it is the only apparent neurological disorder, with or without a family history) or may be brought about by secondary causes (such as physical trauma) and is often attributed to nervous system damage caused by a stroke, disease or trauma. A rare disorder that can occur at any age, even during infancy, cervical dystonia most often occurs in middle-aged individuals, and is more prevalent in women than men. Those with a family history of cervical dystonia or some other type of dystonia are at higher risk of developing the disorder.

Cervical dystonia is the third most common movement disorder following essential tremor and Parkinson's disease. An estimated 3 in every 10,000 people are known to suffer from cervical dystonia. The number of cases reported in North America alone is approximately 300,000.

Symptoms generally begin gradually and then reach a plateau where the symptoms don't get substantially worse. Unfortunately, there is no cure for cervical dystonia and the condition greatly impacts an individual's quality of life. In some cases, the disorder resolves without treatment, but sustained remissions are fairly uncommon.

The type A form of botulinum toxin is reported to be the most lethal natural biological agent known to man. Spores of *C. botulinum* are found in soil and can grow in improperly sterilized and sealed food containers. Botulism, which may be fatal, may be caused by the ingestion of the bacteria. Botulinum toxin acts to produce paralysis of muscles by preventing synaptic transmission by inhibiting the release of acetylcholine across the neuromuscular junction, and is thought to act in other ways as well. Its action essentially blocks signals that normally would cause muscle spasms or contractions, resulting in paralysis. During the last decade, botulinum toxin's muscle paralyzing activity has been harnessed to achieve a variety of therapeutic effects. Controlled administration of botulinum toxin has been used to provide muscle paralysis to treat a variety of medical conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temporomandibular joint disorder, and various types of muscle cramping and spasms. More recently, the muscle-paralyzing effects of botulinum toxin have been applied to therapeutic and cosmetic facial applications such as treatment of wrinkles, frown lines, and other results of spasms or contractions of facial muscles.

In addition to the type A form of botulinum toxin, there are seven other serologically distinct forms of botulinum toxin that are also produced by the gram-positive bacteria *Clostridium botulinum*. Of these eight serologically distinct types of botulinum toxin, the seven that can cause paralysis have been designated botulinum toxin serotypes A, B, C, D, E, F and G. Each of these is distinguished by neutralization with type-specific antibodies. The molecular weight of each of the botulinum toxin proteins is about 150 kD. Due to the molecule size and molecular structure of botulinum toxin, it cannot cross stratum corneum and the multiple layers of the underlying skin architecture. The different serotypes of botulinum toxin vary in the effect and in the severity and duration of the paralysis they evoke in different animal species. For example, in rats, it has been determined that botulinum toxin type A is 500 times more potent than botulinum toxin type B, as measured by the rate of paralysis. Additionally, botulinum toxin type B has been determined to be non-toxic in primates at a dose of 480 U/kg, about 12 times the primate $LD_{50}$ for type A.

As released by *Clostridium botulinum* bacteria, botulinum toxin is a component of a toxin complex containing the approximately 150 kD botulinum toxin protein molecule along with associated non-toxin proteins. These endogenous non-toxin proteins are believed to include a family of hemagglutinin proteins, as well as non-hemagglutinin protein. The non-toxin proteins have been reported to stabilize the botulinum toxin molecule in the toxin complex and protect it against denaturation by digestive acids when toxin complex is ingested. Thus, the non-toxin proteins of the toxin complex protect the activity of the botulinum toxin and thereby enhance systemic penetration when the toxin complex is administered via the gastrointestinal tract. Additionally, it is believed that some of the non-toxin proteins specifically stabilize the botulinum toxin molecule in blood.

The presence of non-toxin proteins in the toxin complexes typically causes the toxin complexes to have molecular weights that are greater than that of the bare botulinum toxin molecule, which is about 150 kD, as previously stated. For example, *Clostridium botulinum* bacteria can produce botulinum type A toxin complexes that have molecular weights of about 900 kD, 500 kD or 300 kD. Botulinum toxin types B and C are produced as complexes having a molecular weight of about 700 kD or about 500 kD. Botulinum toxin type D is produced as complexes having molecular weights of about 300 kD or 500 kD. Botulinum toxin types E and F are only produced as complexes having a molecular weight of about 300 kD.

To provide additional stability to botulinum toxin, the toxin complexes are conventionally stabilized by combining the complexes with albumin during manufacturing. For example, BOTOX® (Allergan, Inc., Irvine, CA) is a botulinum toxin-containing formulation that contains 100 U of type A botulinum toxin with accessory proteins, 0.5 milligrams of human albumin, and 0.9 milligrams of sodium chloride. The albumin serves to bind and to stabilize toxin complexes in disparate environments, including those associated with manufacturing, transportation, storage, and administration.

Typically, the botulinum toxin is administered to patients by carefully controlled injections of compositions containing botulinum toxin complex and albumin. However, there are several problems associated with this approach. Not only are the injections painful, but typically large subdermal wells of toxin are locally generated around the injection sites, in order to achieve the desired therapeutic or cosmetic effect. The botulinum toxin may migrate from these subdermal wells to cause unwanted paralysis in surrounding areas of the body. This problem is exacerbated when the area to be treated is large and many injections of toxin are required to treat the area. Moreover, because the injected toxin complexes contain non-toxin proteins and albumin that stabilize the botulinum toxin and increase the molecular weight of the toxin complex, the toxin complexes have a long half-life in the body and may cause an undesirable antigenic response in the patient. For example, some patients will, over time, develop an allergy to the albumin used as a stabilizer in current commercial formulations. Also, the toxin complexes may induce the immune system of the patient to form neutralizing antibodies, so that larger amounts of toxin are required in subsequent administrations to achieve the same effect. When this happens, subsequent injections must be carefully placed so that they do not release a large amount of toxin into the bloodstream of the patient, which could lead to fatal systemic poisoning, especially since the non-toxin proteins and albumin stabilize the botulinum toxin in blood.

In view of the drawbacks associated with current botulinum toxin formulations, it would be highly desirable to have an injectable botulinum toxin formulation that is efficacious and stable, but exhibits reduced antigenicity and a lower tendency to diffuse locally after injection. It would also be desirable to use such a botulinum toxin formulation for therapeutic purposes to treat cervical dystonia.

Treatments for cervical dystonia include oral medications, botulinum toxin injections, surgery, and complementary therapies. The most commonly prescribed treatment for cervical dystonia is the use of botulinum toxin, typically type A (although Type B has also been used), which can reduce its signs and symptoms. Botulinum toxin can help block the communication between the nerve and the muscle and may alleviate abnormal movements and postures. The number of injections is typically based on the severity of the dystonia. Doctors injecting the toxin may select the muscles to be injected by observing abnormal postures or movements and feeling for the muscle spasm or by using an electromyography machine to measure muscle activity. Each muscle affected by dystonia typically has to be injected separately. As such, based on the diffusion characteristics of currently available toxin formulations, there is a limit to the total quantity of toxin that can be injected into the body at one time. While the treatment for cervical dystonia involves regular neurological intervention, which takes effect over a period of 4-7 days or longer after injection, the response to the treatment with botulinum toxin typically wears off after a 12 week period, often as early as at 10 weeks, requiring the person suffering from cervical dystonia to be injected again. Therefore, a durable, longer acting treatment requiring fewer neurological interventions would be desirable.

SUMMARY OF THE INVENTION

In one of its aspects, the invention relates to a method for producing a biologic effect in the treatment of cervical dystonia by injecting an effective amount, preferably a therapeutically effective amount, of the compositions of this invention to a subject or patient in need of such treatment.

In another of its aspects, this invention provides a method of treating cervical dystonia in an individual in need thereof, the method comprising administering to the individual an injection of a composition comprising: a botulinum toxin, a botulinum toxin complex, or a reduced botulinum toxin complex and a positively charged carrier comprising a positively charged polylysine backbone having covalently attached thereto one or more positively charged efficiency groups having an amino acid sequence of (gly)p-RGRDDRRQRRR-(gly)q (SEQ ID NO: 1), (gly)p-YGRKKRRQRRR-(gly)q (SEQ ID NO: 2) or (gly)p-RKKRRQRRR-(gly)q (SEQ ID NO: 3), wherein the subscripts p and q are each independently an integer of from 0 to 20; and a pharmaceutically acceptable diluent for injection; wherein the botulinum toxin is administered to the individual in an amount from about 100 U to about 450 U; wherein the positively charged carrier is non-covalently associated with the botulinum toxin, botulinum toxin complex, or reduced botulinum toxin complex component; and wherein injection of the composition provides a treatment having at least about a six month to about a 10 month duration of effect in reducing the symptoms of cervical dystonia, thereby extending treatment interval duration for the individual.

In another of its aspects, this invention provides injectable compositions comprising botulinum toxin non-covalently associated with a positively charged carrier molecule used to treat cervical dystonia. In preferred embodiments, the compositions of the invention possess one or more advantages over conventional commercial botulinum toxin formulations, such as BOTOX® or MYOBLOC®. For instance, in certain embodiments, the compositions may exhibit one or more advantages over conventional injectable botulinum formulations, including reduced antigenicity, a reduced tendency to undergo diffusion into surrounding tissue following injection, increased duration of clinical efficacy or enhanced potency relative to conventional botulinum toxin formulations, faster onset of clinical efficacy, and/or improved stability.

A further aspect of this invention is the recognition that certain non-native molecules (i.e., molecules not found in botulinum toxin complexes obtained from *Clostridium botulinum* bacteria) can be added to botulinum toxin, botulinum toxin complexes, and in particular reduced botulinum toxin complexes (as defined herein), to improve toxin diffusion through tissues in the treatment of cervical dystonia. The non-native molecules associate non-covalently with the toxin and act as penetration enhancers that improve the ability of the toxin to reach target structures after injection. Furthermore, the non-native molecules may increase the stability of the toxin prior to and after injection. By way of example, the penetration enhancers may be positively charged carriers, such as cationic peptides, which have no inherent botulinum-toxin-like activity and which also contain one or more protein transduction domains as described herein.

Another aspect of this invention is to provide a composition comprising botulinum toxin, a botulinum toxin complex (or a reduced protein botulinum toxin complex including just the 150 kD neurotoxin itself, or the neurotoxin with some, but not all, of the native complex proteins) and a positively charged carrier for use in a method of treatment for cervical dystonia.

In another aspect, the invention provides effective doses and amounts of the compositions of this invention in the treatment of cervical dystonia that afford a long-lasting, sustained efficacy e.g., a response rate of long duration, following administration by injection to a subject or patient in need of treatment. Such doses and amounts are preferably therapeutically effective doses and amounts that produce or result in a desired therapeutic effect in a subject to whom the doses and amounts are administered. In particular embodiments, a single treatment of a subject or patient with a composition of the invention comprising a botulinum toxin, such as botulinum toxin A, and a positively charged carrier, as described herein, in therapeutically effective dose amounts of about 100 U to about 450 U per subject, afforded a response rate of in the reduction of cervical dystonia symptoms for at least 16 weeks, at least 20 weeks, at least 24 weeks, or about 6 to 10 months, or even longer. Moreover, the compositions of the invention provide an attribute of reduced diffusion or spread from the injection site following injection, thereby localizing the toxin and its effect where desired and decreasing nonspecific or unwanted effects of the toxin at sites or locations distant from the site of injection for treatment.

The duration of effect provided by compositions of the invention, e.g., RT002 as well as by the described treatment methods and uses, affords significant advantages compared to the art. By way of example, subjects undergoing treatment with compositions containing botulinum toxin consider that duration of effect following treatment is of high importance to them. Such a long, sustained duration of effect, which is achieved by even a single treatment with an effective dose and treatment regime of a product of the invention, for example, RT002, permits fewer injections per treatment course for a subject, which is extremely important for the subject. A prolonged duration effect from a single treatment with a product which has clear efficacy and safety, as provided by the inventive compositions and methods described herein, offer less discomfort, less cost and more convenience to subjects undergoing a course of treatment. Furthermore, a product that affords significant and sustained effects, which are maintained for at least a 16 or 24 week period, or for at least a 6-month period, or for greater than a 6-month period, following the single injectable treatment of the product to a subject, provides a solution to an unmet need in the art for both practitioners and patients alike. Thus, the compositions and methods of the invention provide a solution to the problem of too frequent treatments and improve patients' overall well-being. Such prolonged duration of action provides for fewer treatments over an entire treatment course.

In another aspect, the invention provides a method of administering botulinum toxin to achieve an extended duration therapeutic effect in an individual suffering from cervical dystonia, in which the method comprises administering by injection a dose of a sterile injectable composition into an area of the individual in need of treatment to achieve the therapeutic effect following a first treatment with the composition; wherein the composition comprises a botulinum toxin, a botulinum toxin complex, or a reduced botulinum toxin complex component and a positively charged carrier component comprising a positively charged polylysine backbone having covalently attached thereto one or more positively charged efficiency groups having an amino acid sequence of (gly)p-RGRDDRRQRRR-(gly)q (SEQ ID NO: 1), (gly)p-YGRKKRRQRRR-(gly)q (SEQ ID NO: 2) or (gly)p-RKKRRQRRR-(gly)q (SEQ ID NO: 3), wherein the subscripts p and q are each independently an integer of from 0 to 20; wherein the botulinum toxin, botulinum toxin complex, or reduced botulinum toxin complex component is administered to the individual in a treatment dose of about 100 U to 450 U; or more specifically, from about 100 U to 200 U or from about 200 U to 300 U or from about 300 U to 450 U, wherein the positively charged carrier is non-covalently associated with the botulinum toxin, botulinum toxin complex, or reduced botulinum toxin complex component; and a pharmaceutically acceptable diluent suitable for injection; and wherein the first treatment dose of the composition administered by injection to the individual achieves the extended duration therapeutic effect having at least about a 6 month to about a 10 month duration of effect, optionally, before a second or subsequent treatment dose is administered.

In another aspect, the invention provides for the treatment of cervical dystonia, a sterile injectable composition comprising a botulinum toxin, a botulinum toxin complex, or a reduced botulinum toxin complex in a dosage amount selected from more than 100 U, from 100 U to 200 U, 200-300 U, or 300-450 U; and a positively charged carrier comprising a positively charged polylysine backbone having covalently attached thereto one or more positively charged efficiency groups having an amino acid sequence of (gly)p-RGRDDRRQRRR-(gly)q (SEQ ID NO: 1), (gly)p-YGRKKRRQRRR-(gly)q (SEQ ID NO: 2) or (gly)p-RKKRRQRRR-(gly)q (SEQ ID NO: 3), wherein the subscripts p and q are each independently an integer of from 0 to 20; and a pharmaceutically acceptable diluent for injection; wherein the positively charged carrier is non-covalently associated with the botulinum toxin, botulinum toxin complex, or reduced botulinum toxin complex component; and wherein the composition provides a therapeutic effect which endures for at least 20 to 24 weeks, or for at least 6 months, or greater than 6 months, e.g., about 6 months to about 10 months, following a treatment of an individual with an effective dose of the injectable composition.

In some embodiments of these above methods and composition, the composition comprises botulinum toxin of serotype A, preferably a serotype A botulinum toxin having a molecular weight of 150 kDa. In an embodiment, the positively charged carrier has the amino acid sequence RKKRRQRRRG-$(K)_{15}$-GRKKRRQRRR (SEQ ID NO: 4). In an embodiment, the botulinum toxin is present in the composition in a dosage amount from more than 100 U, 100-200 U, or 200-300 U or 300-450 U. In an embodiment, the botulinum toxin is present in the composition in a dosage amount selected from the group consisting of 100 U, 200 U, 300 U and 450 U. In an embodiment, the composition reduces the symptoms of cervical dystonia in an individual who has undergone a single treatment by injection of the composition. In certain embodiments, the duration of the treatment effect comprises greater than 6 months; greater than 7 months; greater than 8 months; greater than 9 months; or at least 6 months through 10 months.

In another of its aspects, the invention provides a method of treating an individual suffering from cervical dystonia who is in need of treatment with injectable botulinum toxin, in which the method of treatment comprises a treatment course having multiple treatment intervals with prolonged duration of effect and duration time between each treatment interval, the treatment course comprising: administering by injection an initial treatment dose of a sterile injectable composition into an area of the individual in need of treatment to achieve a therapeutic effect following the initial treatment with the composition; wherein the composition comprises a botulinum toxin, a botulinum toxin complex, or a reduced botulinum toxin complex component and a positively charged carrier component comprising a positively charged polylysine backbone having covalently attached thereto one or more positively charged efficiency groups having an amino acid sequence of (gly)p-RGRDDRRQRRR-(gly)q (SEQ ID NO: 1), (gly)p-YGRKKRRQRRR-(gly)q (SEQ ID NO: 2) or (gly)p-RKKRRQRRR-(gly)q (SEQ ID NO: 3), wherein the subscripts p and q are each independently an integer of from 0 to 20; and a pharmaceutically acceptable diluent suitable for injection; wherein the botulinum toxin, botulinum toxin complex, or reduced botulinum toxin complex component is administered to the individual in a treatment dose of from more than 100 U, 100-200 U, 200-300 U, or 300-450 U; wherein the positively charged carrier is non-covalently associated with the botulinum toxin, botulinum toxin complex, or reduced botulinum toxin complex component; wherein the initial treatment dose of the composition administered by injection to the individual provides a therapeutic duration of effect lasting through at least about 10 months; and administering subsequent treatment doses of the composition by injection to the individual at treatment intervals comprising a duration of greater than or equal to 3 months to at least about 10 months following the initial treatment dose and between each subsequent treatment dose.

In embodiments of the above-described treatment method, the therapeutic effect is treatment of the symptoms of cervical dystonia. In an embodiment, the composition comprises botulinum toxin of serotype A, preferably, botulinum toxin of serotype A having a molecular weight of 150 kDa. In an embodiment, the positively charged carrier is a positively charged peptide having the amino acid sequence RKKRRQRRRG-(K)15-GRKKRRQRRR (SEQ ID NO: 4). In an embodiment, the composition does not locally diffuse from the site of injection following injection. In specific embodiments, the botulinum toxin is administered to the individual in an amount of more than 100 U, 100-200 U, 200-300 U, or 300-450 U. In certain embodiments, the duration of the treatment interval comprises greater than 3 months; greater than 4 months; greater than 5 months; greater than 6 months; greater than 7 months; greater than 8 months; greater than 9 months; or at least 6 months through 10 months.

DESCRIPTION OF THE FIGURES

FIG. 2 shows the Demographics by Cohort in the Study as described in the Example herein.

FIG. 3 shows Number (%) of Subjects with Treatment-Related AE's by Cohort By Preferred Term in the Study as described in the Example herein.

DETAILED DESCRIPTION OF THE INVENTION

Figure 1:
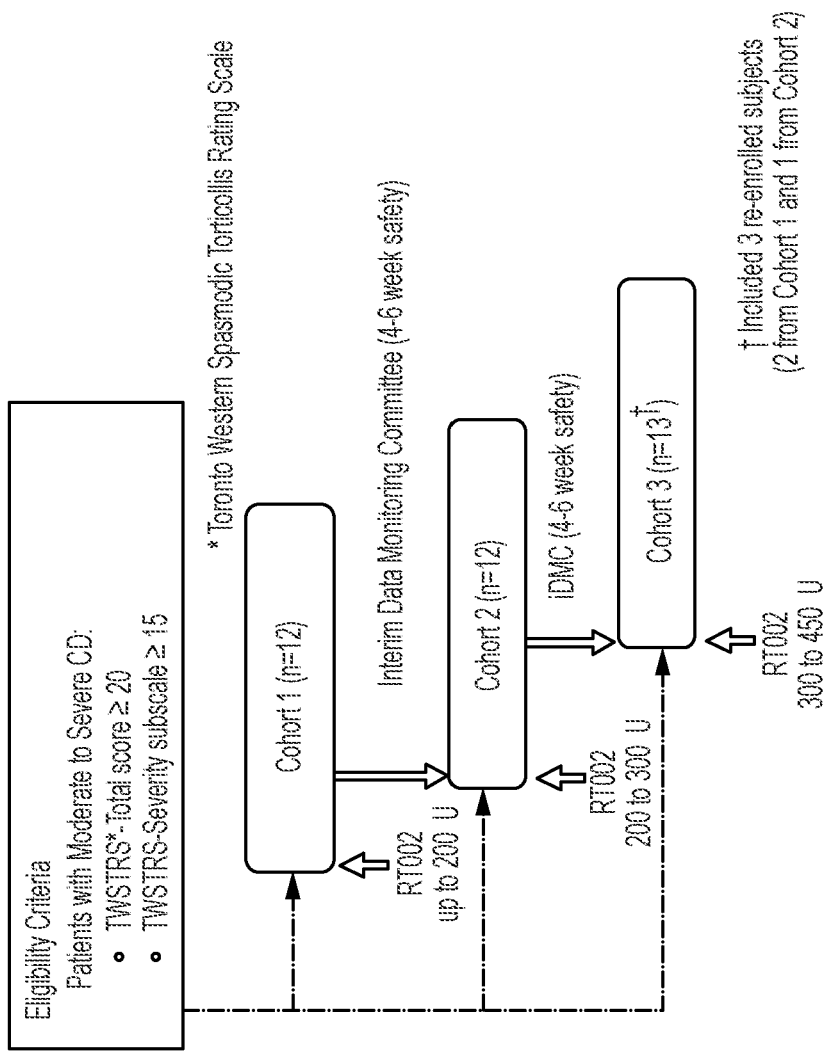
FIG. 1 shows the Cervical Dystonia Phase 2 Study Design as described in the Example herein.

This invention relates to novel injectable compositions comprising botulinum toxin, a botulinum toxin complex, or a reduced botulinum toxin complex used in method to treat cervical dystonia. In preferred embodiments, the compositions stabilize the toxin or enable the transport or delivery of toxin through tissues after injection such that the toxin has reduced antigenicity, a better safety profile, enhanced potency, faster onset of clinical efficacy and/or longer duration of clinical efficacy compared to conventional commercial botulinum toxin complexes that are bound to exogenous albumin (e.g., BOTOX® or MYOBLOC®). The compositions of the invention may be used as injectable applications for providing a botulinum toxin to a subject, for various therapeutic, purposes, as described herein. The compositions of the invention also have an improved safety profile over other compositions and methods of delivery of botulinum toxin. In addition, these compositions can afford beneficial reductions in immune responses to the botulinum toxin. In embodiments, the injectable compositions of the invention provide long lasting efficacy, e.g., an effect lasting at least 20 weeks, at least 24 weeks, at least 6 months, or greater than 6 months, for example, up to about 10 months, in subjects to whom such compositions, particularly those comprising botulinum toxin in amounts of 100 U or more, are administered by injection for the treatment of cervical dystonia.

The term "botulinum toxin" as used herein may refer to any of the known types of botulinum toxin (e.g., 150 kD botulinum toxin protein molecules associated with the different serotypes of *C. botulinum*), whether produced by the bacterium or by recombinant techniques, as well as any such types that may be subsequently discovered including newly discovered serotypes, and engineered variants or fusion proteins. As mentioned above, currently seven immunologically distinct botulinum neurotoxins have been characterized, namely botulinum neurotoxin serotypes A, B, C, D, E, F and G, each of which is distinguished by neutralization with type-specific antibodies. The botulinum toxin serotypes are commercially available, for example, from Sigma-Aldrich (St. Louis, MO) and from Metabiologics, Inc. (Madison, WI), as well as from other sources. The different serotypes of botulinum toxin vary in the animal species that they affect and in the severity and duration of the paralysis they evoke. At least two types of botulinum toxin, types A and B, are available commercially in formulations for treatment of certain conditions. Type A, for example, is contained in preparations of Allergan having the trademark BOTOX® and of Ipsen having the trademark DYSPORT®, and type B is contained in preparations of Elan having the trademark MYOBLOC®.

The term "botulinum toxin" used in the compositions of this invention can alternatively refer to a botulinum toxin derivative, that is, a compound that has botulinum toxin activity but contains one or more chemical or functional alterations on any part or on any amino acid chain relative to naturally occurring or recombinant native botulinum toxins. For instance, the botulinum toxin may be a modified neurotoxin that is a neurotoxin which has at least one of its amino acids deleted, modified or replaced, as compared to a native form, or the modified neurotoxin can be a recombinantly produced neurotoxin or a derivative or fragment thereof. For instance, the botulinum toxin may be one that has been modified in a way that, for instance, enhances its properties or decreases undesirable side effects, but that still retains the desired botulinum toxin activity. Alternatively the botulinum toxin used in this invention may be a toxin prepared using recombinant or synthetic chemical techniques, e.g. a recombinant peptide, a fusion protein, or a hybrid neurotoxin, for example prepared from subunits or domains of different botulinum toxin serotypes (See, U.S. Pat. No. 6,444,209, for instance). The botulinum toxin may also be a portion of the overall molecule that has been shown to possess the necessary botulinum toxin activity, and in such case may be used per se or as part of a combination or conjugate molecule, for instance a fusion protein. Alternatively, the botulinum toxin may be in the form of a botulinum toxin precursor, which may itself be non-toxic, for instance a non-toxic zinc protease that becomes toxic on proteolytic cleavage.

The term "botulinum toxin complex" or "toxin complex" as used herein refers to the approximately 150 kD botulinum toxin protein molecule (belonging to any one of botulinum toxin serotypes A-G), along with associated endogenous non-toxin proteins (i.e., hemagglutinin protein and non-toxin non-hemagglutinin protein produced by *Clostridium botulinum* bacteria). Note, however, that the botulinum toxin complex need not be derived from *Clostridium botulinum* bacteria as one unitary toxin complex. For example, botulinum toxin or modified botulinum toxin may be recombinantly prepared first and then subsequently combined with the non-toxin proteins. Recombinant botulinum toxin can also be purchased (e.g., from List Biological Laboratories, Campbell, CA) and then combined with non-toxin proteins.

This invention also contemplates modulation of the stability of botulinum toxin molecules through the addition of one or more exogenous stabilizers, the removal of endogenous stabilizers, or a combination thereof. For example, this invention contemplates the use of "reduced botulinum toxin complexes", in which the botulinum toxin complexes have reduced amounts of non-toxin protein compared to the amounts naturally found in botulinum toxin complexes produced by *Clostridium botulinum* bacteria. In one embodiment, reduced botulinum toxin complexes are prepared using any conventional protein separation method to extract a fraction of the hemagglutinin protein or non-toxin non-hemagglutinin protein from botulinum toxin complexes derived from *Clostridium botulinum* bacteria. For example, reduced botulinum toxin complexes may be produced by dissociating botulinum toxin complexes through exposure to red blood cells at a pH of 7.3 (e.g., see EP 1514556 A1, hereby incorporated herein by reference). HPLC, dialysis, columns, centrifugation, and other methods for extracting proteins from proteins can be used. Alternatively, when the reduced botulinum toxin complexes are to be produced by combining synthetically produced botulinum toxin with non-toxin proteins, one may simply add less hemagglutinin or non-toxin, non-hemagglutinin protein to the mixture than what would be present for naturally occurring botulinum toxin complexes. Any of the non-toxin proteins (e.g., hemagglutinin protein or non-toxin non-hemagglutinin protein or both) in the reduced botulinum toxin complexes according to the invention may be reduced independently by any amount. In certain exemplary embodiments, one or more non-toxin proteins are reduced by at least about 0.5%, 1%, 3%, 5%, 10%, 20%, 30%, 40%, 50%, 60%, 70%, 80%, 90% or 100% compared to the amounts normally found in botulinum toxin complexes. As noted above, *Clostridium botulinum* bacteria produce seven different serotypes of toxin and commercial preparations are manufactured with different relative amounts of non-toxin proteins (i.e. different amount of toxin complexes). For example, MYOBLOC™ has 5000 U of Botulinum toxin type B per ml with 0.05% human serum albumin, 0.01 M sodium succinate, and 0.1 M sodium chloride. DYSPORT™ has 500 U of botulinum toxin type A-hemagglutinin complex with 125 mcg albumin and 2.4 mg lactose. In certain embodiments, substantially all of the non-toxin protein (e.g., greater than 95%, 96%, 97%, 98% or 99% of the hemagglutinin protein and non-toxin non-hemagglutinin protein) that would normally be found in botulinum toxin complexes derived from *Clostridium botulinum* bacteria is removed from the botulinum toxin complex. Furthermore, although the amount endogenous non-toxin proteins may be reduced by the same amount in some cases, this invention also contemplates reducing each of the endogenous non-toxin proteins by different amounts, as well as reducing at least one of the endogenous non-toxin proteins, but not the others.

As noted above, an exogenous stabilizer (e.g., albumin) is typically added to stabilize botulinum toxin formulations. For instance, in the case of BOTOX®, 0.5 mg of human albumin per 100 U of type A botulinum toxin complex to stabilize the complex. Generally, the amount of exogenous stabilizer that may be added to stabilize the compositions according to the invention is not particularly limited. In some embodiments, the amount of added stabilizer may be less than the amount conventionally added, owing to the ability of positively charged carriers of the invention to act as a stabilizer in its own right. For instance, the amount of added exogenous albumin can be any amount less than the conventional thousand-fold excess of exogenous albumin and, in certain exemplary embodiments of the invention, is only about 0.25, 0.20, 0.15, 0.10, 0.01, 0.005, 0.001, 0.0005, 0.00001, 0.000005, 0.000001, or 0.0000001 mg per 100 U of botulinum toxin. In one embodiment, no exogenous albumin is added as a stabilizer to the compositions of the invention, thus producing albumin-free botulinum toxin compositions.

A preferred composition of the invention is a liquid, botulinum toxin-containing composition that is stabilized without a proteinaceous excipient, especially without any animal protein-derived excipients. Such a liquid composition comprises a botulinum toxin, preferably botulinum toxin of serotype A, a positively charged carrier (e.g., peptide) a non-reducing disaccharide or a non-reducing trisaccharide, a non-ionic surfactant, and a physiologically compatible buffer for maintaining the pH between 4.5. and 7.5. The concentration of the non-reducing sugar in the liquid composition is in the range of 10% through 40% (w/v) and the concentration of the non-ionic surfactant is in the range of 0.005% through 0.5% (w/v). The preferred composition provides a long duration effect after treatment by a single injection In a preferred embodiment, the botulinum toxin A has a molecular weight (MW) of 150 kDa. The preferred composition comprises botulinum toxin, preferably botulinum toxin A, more preferably, of 150 kDa MW, a positively charged carrier (e.g., peptide) as described herein, a non-reducing disaccharide, such as sucrose, a non-ionic surfactant, such as polysorbate 20, polysorbate 40, polysorbate 60, polysorbate 80, or a sorbitan ester, and a physiologically compatible buffer, such as citric acid, acetic acid, succinic acid, tartaric acid, maleic acid, and histidine; and has a pH in the range of pH 4.5. to pH 7.5.

According to the present invention, a positively charged carrier molecule having protein transduction domains or efficiency groups, as described herein, has been found suitable as a transport system for a botulinum toxin, enabling toxin to be injected with improved penetration to target structures such as muscles. The transport occurs without covalent modification of the botulinum toxin. Besides enhancing penetration of botulinum toxin, the positively charged carriers of the invention may, in certain preferred embodiments, stabilize the botulinum toxin against degradation. In such embodiments, the hemagglutinin protein and non-toxin, non-hemagglutinin protein that are normally present to stabilize the botulinum toxin may be reduced or omitted entirely. Similarly, the exogenous albumin that is normally added during manufacturing may be omitted.

By the use of the terms "positively charged" or "cationic" in connection with the term "carrier", it is meant that the carrier has a positive charge under at least some solution-phase conditions, more preferably, under at least some physiologically compatible conditions. More specifically, "positively charged" and "cationic" as used herein, means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" or "cationic" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier (also referred to as a "positively charged backbone") is typically a chain of atoms, either with groups in the chain carrying a positive charge at physiological pH, or with groups carrying a positive charge attached to side chains extending from the backbone. In certain preferred embodiments, the positively charged backbone is a cationic peptide. As used herein, the term "peptide" refers to an amino acid sequence, but carries no connotation with respect to the number of amino acid residues within the amino acid sequence. Accordingly, the term "peptide" may also encompass polypeptides and proteins. In certain preferred embodiments, the positively charged backbone itself will not have a defined enzymatic or therapeutic biologic activity. In certain embodiments, the backbone is a linear hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. The association between the positively charged carrier and the botulinum toxin is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight from about 100 to about 1,500,000, more preferably from about 500 to about 1,200,000, most preferably from about 1000 to about 1,000,000. One of skill in the art will appreciate that when amino acids are used in this portion of the invention, the sidechains can have either the D- or L-form (R or S configuration) at the center of attachment. In certain preferred embodiments, the polypeptide has a molecular weight from about 500 to about 5000, more preferably from 1000 to about 4000, more preferably from 2000 to about 3000. In other preferred embodiments, the polypeptide comprises 10 to 20 amino acids, or 10, 11, 12, 13, 14, 15, 16, 17, 18, 19, or 20 amino acids, preferably polylysine.

Alternatively, the backbone may comprise amino acid analogs and/or synthetic amino acids. The backbone may also be an analog of a polypeptide such as a peptoid. See, for example, Kessler, Angew. Chem. Int. Ed. Engl. 32:543 (1993); Zuckermann et al. Chemtracts-Macromol. Chem. 4:80 (1992); and Simon et al. Proc. Nat'l. Acad. Sci. USA 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the alpha-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene fluoroalkene (—CF═CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In one embodiment, the positively charged backbone is a polypeptide having protein transduction domains (also referred to as efficiency groups). As used herein, an efficiency group or protein transduction domain is any agent that has the effect of promoting the translocation of the positively charged backbone through a tissue or cell membrane. Non-limiting examples of protein transduction domains or efficiency groups include -(gly)$_{n1}$-(arg)$_{n2}$ (SEQ ID NO: 5), HIV-TAT or fragments thereof, or the protein transduction domain (PTD) of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In some embodiments, the HIV-TAT fragment does not contain the cysteine-rich region of the HIV-TAT molecule, in order to minimize the problems associated with disulfide aggregation. Preferably, the fragments of the HIV-TAT and Antennapedia protein transduction domains retain the protein transduction activity of the full protein. Still further preferred are those embodiments in which the HIV-TAT fragment has the amino acid sequence (gly)$_p$-RGRDDRRQRRR-(gly)$_q$ (SEQ ID NO: 1), (gly)$_p$-YGRKKRRQRRR-(gly)$_q$ (SEQ ID NO: 2) or (gly)$_p$-RKKRRQRRR-(gly)$_q$ (SEQ ID NO: 3) wherein the subscripts p and q are each independently an integer of from 0 to 20, or wherein p and q are each independently the integer 1. In another embodiment, the fragment or efficiency group is attached to the backbone via either the C-terminus or the N-terminus of the fragment or amino acid sequence of the efficiency group. In certain preferred embodiments, p is one and q is zero or p is zero and q is one. Preferred HIV-TAT fragments are those in which the subscripts p and q are each independently integers of from 0 to 8, more preferably 0 to 5. In another preferred embodiment the positively charged side chain or branching group is the Antennapedia (Antp) protein transduction domain (PTD), or a fragment thereof that retains activity. These are known in the art, for instance, from Console et al., *J. Biol. Chem.* 278:35109 (2003) and a non-limiting example of an Antennapedia PTD contemplated by this invention is the PTD having the amino acid sequence SGRQIKIWFQNRRMKWKKC (SEQ ID NO: 6). In other embodiments, the positively charged carrier is a positively charged peptide having the amino acid sequence RKKRRQRRR-G-(K)$_{15}$-G-RKKRRQRRR (SEQ ID NO: 4); or a positively charged peptide having the amino acid sequence YGRKKRRQRRR-G-(K)$_{15}$-G-YGRKKRRQRRR (SEQ ID NO: 7); or a positively charged peptide having the amino acid sequences RGRDDRRQRRR-G-(K)$_{15}$-G-RGRDDRRQRRR (SEQ ID NO: 8) for use in the compositions and methods of the invention.

Preferably the positively charged carrier includes side-chain positively charged protein transduction domains or positively charged efficiency groups in an amount of at least about 0.01%, as a percentage of the total carrier weight, preferably from about 0.01 to about 50 weight percent, more preferably from about 0.05 to about 45 weight percent, and most preferably from about 0.1 to about 30 weight %. For positively charged protein transduction domains having the formula -(gly)$_{n1}$-(arg)$_{n2}$ (SEQ ID NO: 5), a preferred range is from about 0.1 to about 25%.

In another embodiment, the backbone portion is a polylysine and positively charged protein transduction domains are attached to the lysine sidechain amino groups or to the C- or N termini. In some preferred embodiments, the polylysine may have a molecular weight that is at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention. In some exemplary embodiments, the polylysine has a molecular weight from about 1,000 to about 1,500,000 D, from about 2,000 to about 800,000 D, or from about 3,000 to about 200,000 D. In other exemplary embodiments, the polylysine has molecular weight from about 100 to about 10,000 D, from about 500 to about 5,000 D, from about 1,000 to about 4,000 D, from about 1,500 to about 3,500 D or from about 2,000 to about 3,000 D. Preferred is a polylysine polypeptide having 10 to 20 lysines (SEQ ID NO: 9), more preferably, 15 lysines. In some embodiments, the polylysine contemplated by this invention can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is preferably from one to four times the combined length of the negatively charged components. Preferred positively charged protein transduction domains or efficiency groups include, for example, -gly-gly-gly-arg-arg-arg-arg-arg-arg-arg (-Gly$_3$Arg$_7$ (SEQ ID NO: 10)) or HIV-TAT.

In another preferred embodiment the positively charged backbone is a polyalkyleneimine, non-limiting examples of which include polyethyleneimine, polypropyleneimine, and polybutyleneimine. In certain embodiments, the polyalkyleneimine has a molecular weight of at least 100, 200, 300, 400, 500, 600, 700, 800, 900, 1000, 1500, 2000, 2500, 3000, 3500, 4000, 4500, 5000, 5500, or 6000 D, and less than about 2,000,000, 1,000,000, 500,000, 250,000, 100,000, 75,000, 50,000, and 25,000 D. Within the range of 100 to 2,000,000 D, it is contemplated that the lower and/or upper range may be increased or decreased, respectively, by 100, with each resulting sub-range being a specifically contemplated embodiment of the invention.

In other embodiments of this invention, the carrier is a relatively short polylysine or polyethyleneimine (PEI) backbone (which may be linear or branched) and which has positively charged branching groups. Without wishing to be constrained by theory, it is believed that such carriers are useful for minimizing uncontrolled aggregation of the backbones and botulinum toxin in a therapeutic composition, which causes the transport efficiency to decrease dramatically. When the carrier is a relatively short linear polylysine or PEI backbone, the backbone will have a molecular weight of less than 75,000 D, more preferably less than 30,000 D, and most preferably, less than 25,000 D. When the carrier is a relatively short branched polylysine or PEI backbone, however, the backbone will have a molecular weight less than 60,000 D, more preferably less than 55,000 D, and most preferably less than 50,000 D.

In one particularly interesting embodiment, the non-native molecules are cationic peptides that have no inherent botulinum-toxin-like activity and that also contain one or more protein transduction domains as described herein. Without wishing to be bound by any particular scientific theory, it is believed that the peptides enhance tissue penetration of molecules associated in complex after injection, while enhancing stabilization of the botulinum toxin in skin and in vitro. It is believed that the enhanced tissue penetration afforded by these peptides in particular affords reduced antigenicity, a better safety profile, enhanced potency, faster onset of clinical efficacy or longer duration of clinical efficacy compared to conventional commercial botulinum toxin complexes that are bound to exogenous albumin (e.g., BOTOX® or MYOBLOC®).

In preferred embodiments, the concentration of positively charged carriers in the compositions according to the invention is sufficient to enhance the delivery of the botulinum toxin to molecular targets such as, for example, motor nerve plates. Furthermore, without wishing to be bound by theory, it is believed that the penetration rate follows receptor-mediated kinetics, such that tissue penetration increases with increasing amounts of penetration-enhancing-molecules up to a saturation point, upon which the transport rate becomes constant. Thus, in a preferred embodiment, the amount of added penetration-enhancing-molecules is equal to the amount that maximizes penetration rate right before saturation. A useful concentration range for the positively charged carrier (or carrier peptide) in the injectable compositions of this invention is about 0.1 pg of carrier per Unit (U) of botulinum toxin (0.1 pg/U) to about 1.0 mg per Unit (mg/U) of the botulinum toxin as described herein. A useful concentration range for the positively charged carrier (or carrier peptide) in the topical compositions of the invention is about 1.0 pg/U to 0.5 mg/U of botulinum toxin (amount of carrier/U of botulinum toxin). In other embodiments, the positively charged carrier (or carrier peptide) is present in the injectable compositions of the invention in the range of, for example, 10 ng/U to 200 ng/U of botulinum toxin, or in the range of 1 ng/U to 1000 ng/U of botulinum toxin; or in the range of 0.1 ng/U to 10,000 ng/U of botulinum toxin. In some embodiments, the amount of positively charged carrier (or carrier peptide) to Units of botulinum toxin present in the compositions of the invention is, by way of nonlimiting example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, etc. ng of carrier per Unit of botulinum toxin (ng/U). Preferably, the botulinum toxin is of serotype A, and particularly, the 150 kD form of serotype A botulinum toxin.

In general, methods and procedures for measuring the activity of botulinum toxin, i.e., units (U) of botulinum toxin activity, are known to and practiced by those having skill in the art. Briefly, median lethality assays ($LD_{50}$ assays) in mice are conventionally used to estimate the number of units of botulinum toxin with a high degree of precision. Doses of all commercially available botulinum toxins are expressed in terms of units of biologic activity. By way of example, one unit of botulinum toxin corresponds to the calculated median intraperitoneal lethal dose (LD50) in female Swiss-Webster mice. See, Hoffman, R. O. et al., 1986, *Int. Ophthalmol. Clin.*, 26:241-50, as well as DePass, L. R., 1989, *Toxicol. Letters*, 49:159-170; and Pearce, L. B. et al., 1994, *Toxicol. Appl. Pharmacol.*, 128:69-77, which also describe lethality assays in the art. More particularly, a suitable method for determining botulinum toxin units for a botulinum toxin component of the compositions of the invention is as follows: Forty-eight (48) female CD-1 mice weighing 17-23 grams are randomly assigned to six doses of the test article (1.54, 1.31, 1.11, 0.95, 0.80, and 0.68 U/0.5 mL), eight (8) animals per dose group. The test article refers to the botulinum toxin preparation or sample being assayed or tested. The animals are housed eight per cage and are weighed within 24 hours of dosing with the test article. On the day of dosing, the test article is diluted to the appropriate concentrations in isotonic saline (0.9% NaCl). Each animal is administered 0.5 mL of diluted test article via intraperitoneal injection. After injection, mice are returned to the cage and fatalities are recorded daily for three days. Lethality is scored 72 hours post injection and the results are analyzed by probit or logistic analysis to derive the $LD_{50}$ value relative to a reference standard that is assessed using the same dosing regimen. By way of example, the reference standard is a specifically qualified and calibrated lot of the same composition of the invention that is used for comparison to derive relative potency of the test article. The determined $LD_{50}$ value is then corrected for the cumulative dilutions performed to assign a relative potency value for the neat (undiluted) test article.

Compositions of this invention are preferably in a form that permits injection into the skin or epithelium of subjects or patients. The term "in need" is meant to include both pharmaceutical or health-related needs (e.g., treating conditions involving undesirable dystonic contractions or muscle spasms). In preferred embodiments, the compositions are prepared by mixing the botulinum toxin (either containing the associated non-toxin proteins or reduced associated non-toxin proteins) with the positively charged carrier, and usually with one or more additional pharmaceutically acceptable carriers or excipients. In their simplest form, they may contain an aqueous pharmaceutically acceptable diluent, such as buffered saline (e.g., phosphate buffered saline). However, the compositions may contain other ingredients typically found in injectable pharmaceutical or cosmeceutical compositions, including a dermatologically or pharmaceutically acceptable carrier, vehicle or medium that is compatible with the tissues to which it will be applied. The term "pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration.

In terms of their form, compositions of this invention may include solutions, emulsions (including microemulsions), suspensions, gels, powders, or other typical solid or liquid compositions used for injection to muscle and other tissues where the compositions may be used. In preferred embodiments, the compositions of the invention are present in low-viscosity, sterile formulations suitable for injection with a syringe. As used herein, the terms compositions and formulations are essentially interchangeable when referring to the compositions and formulations according to the present invention. The compositions of the invention may be in the form of a lyophilized powder that is reconstituted using a pharmaceutically acceptable liquid diluent prior to injection. In certain embodiments, the lyophilized powder is reconstituted with a liquid diluent to form an injectable formulation with a viscosity of about 0.1 to about 2000 cP, more preferably about 0.2 to about 500 cP, even more preferably about 0.3 to about 50 cP, and even more preferably about 0.4 to about 2.0 cP. The compositions of the invention may contain, in addition to the botulinum toxin and positively charged carrier, other ingredients typically used in such products, such as antimicrobials, hydration agents, tissue bulking agents or tissue fillers, preservatives, emulsifiers, natural or synthetic oils, solvents, surfactants, detergents, gelling agents, antioxidants, fillers, thickeners, powders, viscosity-controlling agents and water, and optionally including anesthetics, anti-itch actives, botanical extracts, conditioning agents, minerals, polyphenols, silicones or derivatives thereof, vitamins, and phytomedicinals.

The injectable compositions according to this invention may be in the form of controlled-release or sustained-release compositions which comprise botulinum toxin and positively charged carrier encapsulated or otherwise contained within a material such that they are released within the tissue in a controlled manner over time. The composition comprising the botulinum toxin and positively charged carrier may be contained within matrixes, liposomes, vesicles, microcapsules, microspheres and the like, or within a solid particulate material, all of which is selected and/or constructed to provide release of the botulinum toxin over time. The botulinum toxin and the positively charged carrier may be encapsulated together (i.e., in the same capsule) or separately (i.e., in separate capsules).

In embodiments, compositions of the invention comprise liquid (aqueous) compositions (or formulations) comprising a botulinum toxin as described herein, a positively charged carrier (or peptide) as described herein, a non-reducing disaccharide or a non-reducing trisaccharide, a non-ionic surfactant, and a physiologically compatible buffer, which is capable of maintaining a suitable pH, such as a pH in the range of pH 4.5 to pH 7.5, or pH 4.5 to pH 6.8, or pH 4.5 to pH 6.5. It is to be understood that a suitable pH also includes the upper and lower pH values in the range, e.g., a pH of 6.5 or a pH of 7.5. The concentration of the non-reducing sugar in the liquid composition is in the range of 10% through 40% (w/v) and the concentration of the non-ionic surfactant is in the range of 0.005% through 0.5% (w/v). The liquid compositions may be dried, preferably by lyophilization, to produce stabilized solid compositions, which may thereafter be reconstituted for use, for example, using sterile saline or other known physiologically and pharmaceutically acceptable diluents, excipients, or vehicles, especially those known for use in injectable formulations. Preferably, the dried, e.g., lyophilized, solid compositions are noncrystalline and amorphous solid compositions, and may be in the form of powders, for example. Also, preferably, the compositions of the invention do not include animal protein-derived products, such as albumin. Compositions that are suitable for the invention are also described in U.S. Application Publication No. US 2010/0330123, the entire contents of which are incorporated herein by reference. In particular embodiments the compositions comprise botulinum toxin of serotype A. In other particular embodiments, the compositions comprise botulinum toxin of serotype A which has a molecular weight of 150 kDa.

In certain embodiments, the compositions of the invention contain a non-reducing sugar, which is preferably a disaccharide, non-limiting examples of which include trehalose, including its anhydrous and hydrated forms, or sucrose, as well as combinations thereof. In some embodiments, the hydrated form of trehalose, trehalose-dihydrate, is preferable. In other embodiments, the compositions contain a trisaccharide, a non-limiting example of which is raffinose. In general, the concentration of the non-reducing sugar, preferably a disaccharide, e.g., sucrose, in the compositions of the invention are in the range of 10% to 40% (w/v), preferably 10% to 25% (w/v), more preferably 15% to 20% (w/v). In some preferred embodiments, the concentration of the non-reducing sugar, preferably a disaccharide, e.g., sucrose, is 10%, 11%, 12%, 13%, 14%, 15%, 16%, 17%, 18%, 19% or 20% (w/v).

In general, the compositions of the invention may include any non-ionic surfactant that has the ability to stabilize botulinum toxin and that is suitable for pharmaceutical use. In some embodiments, the non-ionic surfactant is a polysorbate, such as, by way of nonlimiting example, polysorbate 20, polysorbate 40, polysorbate 60, and polysorbate 80. In other embodiments, the non-ionic surfactant is a sorbitan ester, non-limiting examples of which include SPAN® 20, SPAN® 60, SPAN® 65, and SPAN® 80. The non-ionic surfactants Triton® X-100 or NP-40 may also be used. In addition, a combination of the different non-ionic surfactants may be used. In certain preferred embodiments, the non-ionic surfactant is a polysorbate, a poloxamer and/or a sorbitan; polysorbates and sorbitans are particularly preferred. In embodiments, the non-ionic surfactant is present in the compositions of the invention in the range of 0.005% to 0.5%, or in the range of 0.01% to 0.2%, or in the range of 0.02% to 0.1% or in the range of 0.05 to 0.08%, inclusive of the upper and lower values. In addition, the compositions of the invention may contain a non-ionic surfactant in the amount of 0.01%, 0.02%, 0.03%, 0.04%, 0.05%, 0.06%, 0.07%, 0.08%, 0.09%, 0.10%, 0.11%, 0.12%, 0.13%, 0.14%, or 0.15%.

In general for the compositions of the invention, any physiologically compatible buffer capable of maintaining the pH in the above ranges is suitable for use. Non-limiting examples of such buffers include salts of citric acid, acetic acid, succinic acid, tartaric acid, maleic acid, and histidine. Non-limiting examples of suitable buffer concentrations include buffer concentrations in the range of 0.400% to 0.600%; 0.450% to 0.575%, or 0.500% to 0.565%. The compositions of the invention may also comprise a mixture of buffer salts, non-limiting examples of which include citrate/acetate, citrate/histidine, citrate/tartrate, maleate/histidine, or succinate/histidine. Accordingly, a composition of the invention which provides a long duration effect after treatment by a single injection includes a botulinum toxin, such as botulinum toxin A or botulinum toxin A of 150 kDa MW, as described herein, a positively charged carrier (or peptide) as described herein, a non-reducing disaccharide, such as sucrose, a non-ionic surfactant, such as polysorbate 20, polysorbate 40, polysorbate 60, polysorbate 80, or a sorbitan ester, and a physiologically compatible buffer, such as citric acid, acetic acid, succinic acid, tartaric acid, maleic acid, and histidine, which is capable of maintaining a suitable pH, such as a pH in the range of pH 4.5 to pH 6.5 or in the range of pH 4.5. to pH 7.5, in w/v amounts as described herein.

A particular composition of the invention is an albumin-free, liquid (aqueous) composition which comprises a botulinum toxin, preferably botulinum toxin of serotype A, or a botulinum toxin A having a molecular weight of 150 kDa; a positively charged carrier (e.g., peptide); a non-reducing disaccharide or a non-reducing trisaccharide, preferably a disaccharide, present in a range of 10% through 40% (w/v); a non-ionic surfactant, preferably, a polysorbate or sorbitan ester, present in the range of 0.005% through 0.5% (w/v); and a physiologically compatible buffer, such as citric acid, acetic acid, succinic acid, tartaric acid, maleic acid, or histidine, present in the range of 0.400% to 0.600%; 0.450% to 0.575%, or 0.500% to 0.565%, for maintaining the pH between 4.5. and 7.5.

Botulinum toxin formulations according to the invention can be delivered by injection (typically using a syringe) to muscles underlying the skin, or to glandular structures within the skin, in an effective amount to produce paralysis, produce relaxation, alleviate contractions, prevent or alleviate spasms, reduce glandular output, or other desired effects. Local delivery of the botulinum toxin in this manner could afford dosage reductions, reduce toxicity and allow more precise dosage optimization for desired effects relative to injectable or implantable materials.

The compositions of the invention are administered to deliver an effective amount, preferably a therapeutically effective amount, of the botulinum toxin. The term "effective amount" or "therapeutically effective amount" as used herein means an amount of a botulinum toxin as defined above that is sufficient to produce the desired muscular paralysis or other biological effect, but that implicitly is a safe amount, i.e., one that is low enough to avoid serious side effects.

The compositions of the invention may contain an appropriate effective amount of the botulinum toxin for application as a single-dose treatment, or may be more concentrated, either for dilution at the place of administration or for use in multiple applications and/or sequential applications over periods of time. Through the use of the positively charged carrier this invention, a botulinum toxin can be administered by injection to a subject for treating conditions such as cervical dystonia. The botulinum toxin is administered by injection to muscles or to other skin-associated or other target tissue structures.

Most preferably, the compositions are administered by or under the direction of a physician or other health care professional. They may be administered in a single treatment or in a series of treatments over time. In preferred embodiments, a composition according to the invention is injected at a location or locations where an effect associated with botulinum toxin is desired. In the treatment of cervical dystonia, the following Table 1 provides guidance as to the appropriate dosage of RTT150 (the RT002 product is composed of purified 150 kDa botulinum neurotoxin, referred to as RTT150) by dose ranges 1, 2 and 3 for specified muscle groups:

[Table 1 was created using the perspective of the recommended dosing ranges for BOTOX® by involved muscle (Allergan, Inc. BOTOX® US Prescribing Information, 2015 & BOTOX® medical website, Flexible dosing in cervical dystonia. https://www.botoxmedical.com/CervicalDystonia/DosingAndAdministration)]

TABLE 1

General Guideline on Dosing Ranges by Muscle for Cervical Dystonia, RTT150 for Injection -

|  | Dose Range 1 | Dose Range 2 | Dose Range 3 |
| --- | --- | --- | --- |
| Total maximum dose | Per subject: up to 200 U RTT150 | Per subject: 200 to 300 U RTT150 | Per subject: 300 to 450 U RTT150 |
| By muscle | Recommended dose range RTT150 Units | Recommended dose range RTT150 Units | Recommended dose range RTT150 Units |
| Splenius capitis | 15-100 a | 15-100 | 22.5-150 |
| Sternocleidomastoid | 15-100 a | 15-100 a | 22.5-100 a |
| Levator scapulae | 20-100 a | 20-100 a | 30-150 |
| Scalene complex | 15-50 a | 15-50 a | 22.5-75 |
| Semispinalis capitis | 30-100 a | 30-100 a | 45-150 |
| Longissimus | 30-100 a | 30-100 a | 45-150 |
| Trapezius | 20-100 a | 20-100 a | 30-150 |
| Splenius cervicis | 20-60 a | 20-60 a | 30-90 |

Because of its nature, the botulinum toxin preferably is administered at an amount, application rate, and frequency that will produce the desired result without producing any adverse or undesired results. In embodiments, a single treatment with an effective dose of the compositions of the invention affords an effect of long duration such that during a course of treatment for an indication treatable by botulinum toxin, or series of injections during a single multiple treatment session, with a concomitant effect that endures over extended periods of time, e.g., at least 6 months or greater than 6 months, namely, 6 months, 7 months, 8 months, 9 months, or longer, including 10 months. The longer duration of action provides for longer intervals or time periods between treatments where multiple treatments are used to maintain a treatment goal or effect. In an embodiment, the longer duration of effect of the composition following administration to, or dosing of, an individual with a composition of the invention providing about 100 U to 450 U; or more specifically, from about 100 U to 200 U or from about 200 U to 300 U or from about 300 U to 450 U, of botulinum toxin, for example, at least 6 months or greater than 6 months, such as 7, 8, 9, or 10 months, including in between, is relative to a duration of effect of a botulinum toxin-containing composition or product that does not contain a positively charged carrier (or peptide) according to the present invention. In some cases, a composition or product containing botulinum toxin without a positively charged carrier (or peptide) of the invention is effective for less than 6 months, such as 3 or 4 months.

In certain embodiments, the compositions of the invention, which comprise a botulinum toxin and a positively charged carrier comprising a positively charged polymeric backbone with one or more covalently attached positively charged efficiency groups as described herein, are administered as a single injection to a subject or patient in need thereof in an amount or at a dose which provides about 100 U to 450 U; or more specifically, from about 100 U to 200 U or from about 200 U to 300 U or from about 300 U to 450

U, of botulinum toxin per treatment dose per subject for the treatment of cervical dystonia. According to the invention, a treatment effect endures for several weeks or months, for example, for at least 10 weeks, for at least 12 weeks, for at least 16 weeks, for at least 20 weeks, for at least 24 weeks, or for at least 6 months, or greater than 6 months, such as 6, 7, 8, 9, or 10 months, or longer. In embodiments, the botulinum toxin is of serotype A, B, C, D, E, F, or G. In an embodiment, the botulinum toxin is of serotype A. In an embodiment, the serotype A botulinum toxin has a molecular weight of 150 kDa. In an embodiment, the serotype A botulinum toxin is in the form of a higher molecular weight complex as described supra. In preferred embodiments, the 150 kDa botulinum toxin or the higher molecular weight forms of the toxin are in albumin-free formulations. In an embodiment, the positively charged polymeric backbone is polylysine or polyethyleneimine. In an embodiment, the one or more positively charged efficiency groups include -(gly)$_{n1}$-(arg)$_{n2}$ (SEQ ID NO: 5), in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In some embodiments, the one or more positively charged efficiency groups has the amino acid sequence (gly)$_p$-RGRDDRRQRRR-(gly)$_q$ (SEQ ID NO: 1), (gly)$_p$-YGRKKRRQRRR-(gly)$_q$ (SEQ ID NO: 2) or (gly)$_p$-RKKRRQRRR-(gly)$_q$ (SEQ ID NO: 3), wherein the subscripts p and q are each independently an integer of from 0 to 20. In certain preferred embodiments, p is one and q is zero or p is zero and q is one. In other preferred embodiments, the subscripts p and q are each independently integers of from 0 to 8, more preferably 0 to 5. In a particular embodiment, the positively charged carrier has the amino acid sequence RKKRRQRRRG-(K)$_{15}$-GRKKRRQRRR (SEQ ID NO: 4). In other embodiments, the one or more positively charged efficiency groups is attached to the positively charged backbone via either the C-terminus or the N-terminus of the efficiency group, e.g., amino acid sequence. In some embodiments, the one or more positively charged efficiency groups are attached to either end, or both ends, of the positively charged polylysine backbone of the positively charged carrier. In particular embodiments, the positively charged backbone is polylysine and the botulinum toxin is of serotype A. In another particular embodiment, the serotype A botulinum toxin has a molecular weight of 150 kDa, the positively charged backbone is polylysine and the one or more covalently attached positively charged efficiency groups has the amino acid sequence (gly)$_p$-RGRDDRRQRRR-(gly)$_q$ (SEQ ID NO: 1), (gly)$_p$-YGRKKRRQRRR-(gly)$_q$ (SEQ ID NO: 2) or (gly)$_p$-RKKRRQRRR-(gly)$_q$ (SEQ ID NO: 3), wherein the subscripts p and q are each independently an integer of from 0 to 20, or are each independently the values as set forth above; or the positively charged carrier has the amino acid sequence RKKRRQRRRG-(K)$_{15}$-GRKKRRQRRR (SEQ ID NO: 4). In embodiments, the composition is administered by injection in an amount or dose that provides 20 U or at least 20 U; 30 U or at least 30 U; 40 U or at least 40 U; 50 U or at least 50 U; 60 U or at least 60 U; 70 U or at least 70 U; 80 U or at least 80 U; 90 U or at least 90 U; or 100 U or at least 100 U of botulinum toxin per injection. Amounts or doses between the foregoing amounts or doses are also contemplated, for example, 25 U or at least 25 U; 35 U or at least 35 U; 45 U or at least 45 U, and the like. In particular embodiments, the composition is administered by injection as a single treatment dose in an amount that provides about 100 U to 450 U; or more specifically, from about 100 U to 200 U or from about 200 U to 300 U or from about 300 U to 450 U, of botulinum toxin and a response or effect is achieved and maintained for a long duration, e.g., for at least 10 weeks, for at least 12 weeks, for at least 16 weeks, for at least 20 weeks, at least 24 weeks, at least 6 months, or greater than 6 months, such as, for example, 6, 7, 8, 9, or 10 months, or longer.

Without wishing to be limiting, in a course of treatment, the compositions of the invention may be administered at less frequent intervals following an initial treatment dose based on the extended duration of effect afforded by the therapeutically effective doses of the compositions and methods of the invention as described herein. For example, the compositions of the invention may be administered (or dosed) to an individual in need about twice per year (about every 6 months), or every 7 months, 8 months, 9 months, or 10 months, or longer, by the practice of the methods of the invention. In a particular embodiment, an individual is administered a dose of a composition of the invention twice per year. A median duration between doses may be 6 months, at least 6 months, or greater than 6 months, depending on the therapeutic treatment and/or the desire for treatment as determined by the individual being treated. Thus, dosing of an individual with the compositions of the invention may occur twice a year or longer than twice a year, and for example, every 6, 7, 8, 9, or 10 months, after an initial dose. A composition of the invention may be dosed at the appropriate interval at about 100 U to 450 U; or more specifically, from about 100 U to 200 U or from about 200 U to 300 U or from about 300 U to 450 U, of botulinum toxin in the composition.

This invention also contemplates the use of a variety of delivery devices for injecting botulinum toxin-containing compositions described herein across skin. Such devices may include, without limitation, a needle and syringe, or may involve more sophisticated devices capable of dispensing and monitoring the dispensing of the composition, and optionally monitoring the condition of the subject in one or more aspects (e.g., monitoring the reaction of the subject to the substances being dispensed).

In some embodiments, the compositions can be pre-formulated and/or pre-installed in a delivery device as such. This invention also contemplates embodiments wherein the compositions are provided in a kit that stores one or more components separately from the remaining components. For example, in certain embodiments, the invention provides for a kit that separately stores botulinum toxin and the positively charged carrier for combining at or prior to the time of application. The amount of positively charged carrier or the concentration ratio of these molecules to the botulinum toxin will depend on which carrier is chosen for use in the composition in question. The appropriate amount or ratio of carrier molecule in a given case can readily be determined, for example, by conducting one or more experiments such as those described below.

In general, the invention also contemplates a method for administering botulinum toxin (alternatively as botulinum toxin complexes or reduced botulinum toxin complexes) to a subject or patient in need thereof, in which an effective amount of botulinum toxin is administered in conjunction with a positively charged carrier, as described herein. By "in conjunction with" it is meant that the two components (botulinum toxin and positively charged carrier) are administered in a combination procedure, which may involve either combining them prior to administration to a subject, or separately administering them, but in a manner such that they act together to provide the requisite delivery of an effective amount of the therapeutic protein. For example, a composition containing the positively charged carrier may first be administered to the skin of the subject, followed by application a skin patch, syringe, or other device containing the botulinum toxin. The botulinum toxin may be stored in dry form in a syringe or other dispensing device and the positively charged carrier may be injected before application of the toxin so that the two act together, resulting in the desired tissue penetration enhancement. In that sense, thus, the two substances (positively charged carrier and botulinum toxin) act in combination or perhaps interact to form a composition or combination in situ. Accordingly, the invention also includes a kit with a device for dispensing botulinum toxin and a liquid, gel, or the like that contains the positively charged carrier, and that is suitable for injection to the skin or target tissue of a subject. Kits for administering the compositions of the inventions, either under direction of a health care professional or by the patient or subject, may also include a custom applicator suitable for that purpose.

The compositions of this invention are suitable for use in physiologic environments with pH ranging from about 4.5 to about 6.3, and may thus have such a pH. However, compositions having a pH ranging from about 4.5 to about 7.5 are also embraced by the invention as described herein. The compositions according to this invention may be stored either at room temperature or under refrigerated conditions.

In some embodiments, the patient to be treated is 65 years of age, at least 65 years old, or over 65 years old. For example, the patient may be 65, 66, 68, 70, 75, 80 years, or older.

EXAMPLES

Example 1

This example is an open-label, sequential, dose-escalating clinical study of DaxibotulinumtoxinA Injectable (RT002) to treat moderate-to-severe isolated cervical dystonia, a movement disorder of the neck, in adults. Thirty-seven subjects with moderate-to-severe cervical dystonia were enrolled at multiple sites in the United States. The trial's first cohort of 12 subjects received a single dose of up to 200 units of RT002 injectable, the second cohort of 12 subjects received between 200 and 300 units, and the third cohort of 13 subjects received from 300 to 450 units. The study showed positive efficacy results and that RT002 was generally safe and well-tolerated.

All subjects were followed until they returned to baseline or for up to a total of 24 weeks after treatment. Due to the long duration of effect seen in the first cohort, subjects in the second and third cohorts were given the option to continue. Several patients elected to remain in the study and will be followed for up to 36 weeks.

The primary efficacy endpoint of the Phase 2 study was an improvement in dystonia symptoms as measured by change (reduction) from baseline in Toronto Western Spasmodic Torticollis Rating Scale (TWSTRS)-Total score at four weeks. TWSTRS is a validated composite scale that covers different features of the cervical dystonia condition. The first part of the scale is based on the physical findings and severity of dystonia, the second part rates the patient's perceived level of disability, and the third part rates pain associated with the condition. The study protocol also feature a number of secondary efficacy endpoints.

In sum, the Study Objectives were:
To assess the safety and preliminary efficacy of RT002 for Injection in subjects with isolated Cervical Dystonia and
To evaluate the duration of effect of RT002 for Injection in the treatment of isolated Cervical Dystonia
The Primary Endpoint was:
improvement of dystonia, as measured by change from baseline in TWSTRS-Total score at Week 4 (TWSTRS=Toronto Western Spasmodic Torticollis Rating Scale).
The Secondary Endpoints were:
Change from baseline in TWSTRS-Total score;
Change from baseline in TWSTRS subscale scores: (i.e. TWSTRS-Severity Scale, TWSTRS-Disability Scale & TWSTRS-Pain Scale);
Duration of effect, as assessed by the number of weeks from treatment until return of symptoms that warrant treatment, regarded as when a subject reaches or exceeds their target TWSTRS-Total score, or subject expresses a need for treatment and investigator agrees that it is necessary;
Percentage of responders showing improvement on CGIC (Clinician Global Impression of Change); and
Patient-rated quality of life, measured by change from baseline in CDIP-58 (Cervical Dystonia Impact Profile-58) Total score (all post-treatment time points).
Top-Line 24-Week Results:
DURATION OF EFFECT AT LEAST 24 WEEKS: The median duration of effect was at least 24 weeks for each of the three dose cohorts studied. Duration of effect was defined as the number of weeks from treatment until the return of signs and symptoms that warrant retreatment, based on subjects reaching their target Toronto Western Spasmodic Torticollis Rating Scale (TWSTRS) score. For reference, current treatment of cervical dystonia calls for injection of botulinum toxin approximately every 3 months (12 weeks), or 4 times per year.

POSITIVE EFFICACY RESULTS: The trial's 4-week primary efficacy measurement was the improvement in signs and symptoms of cervical dystonia as determined by reduction of the TWSTRS-Total score from baseline. At Week 4, RT002 injectable showed a clinically significant mean reduction of 38% from baseline across all three cohorts. This reduction continued to increase to 50% at Week 6 for all subjects, was 42% at Week 12 and was maintained at or above 30% through Week 24. For reference, placebo-controlled trials for botulinum toxin type A products approved to treat cervical dystonia had a reduction in the TWSTRS-Total score from baseline of 21% to 26% at Week 4 and 13% to 16% at Week 12.

On the key secondary endpoint, percentage of responders showing improvement on Clinician Global Impression of Change (CGIC), 97% of all subjects experienced an improvement in cervical dystonia symptoms at Week 4.

GENERALLY SAFE AND WELL-TOLERATED: In all three cohorts, RT002 injectable appeared to be generally safe and well-tolerated through Week 24. There were no serious adverse events and no dose-dependent increase in adverse events. The treatment-related adverse events were generally transient and mild to moderate in severity, with one case of neck pain reported as severe. The most common adverse events were dysphagia, or difficulty in swallowing (14%), of which all cases were mild in severity, injection site redness (8%), injection site bruising (5%), injection site pain (5%), muscle tightness (5%) and muscle weakness (5%). For reference, trials for botulinum toxin type A products approved to treat cervical dystonia have adverse events for dysphagia ranging from 13% to 39%.

Figure 4:
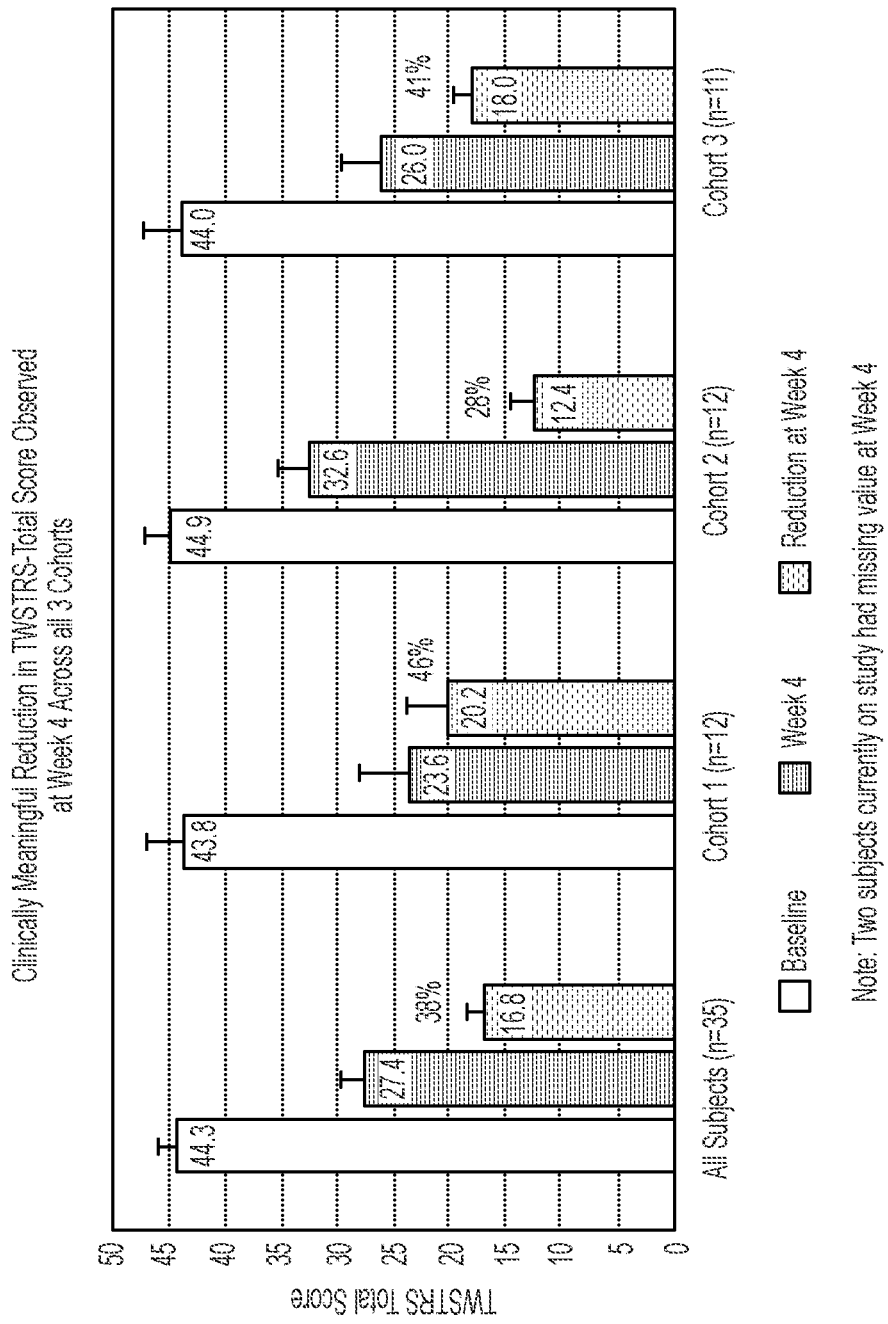
FIG. 4 shows Primary Endpoint by Cohort—Reduction in TWSTRS-Total Score at Week 4 in the Study as described in the Example herein.
Figure 5:
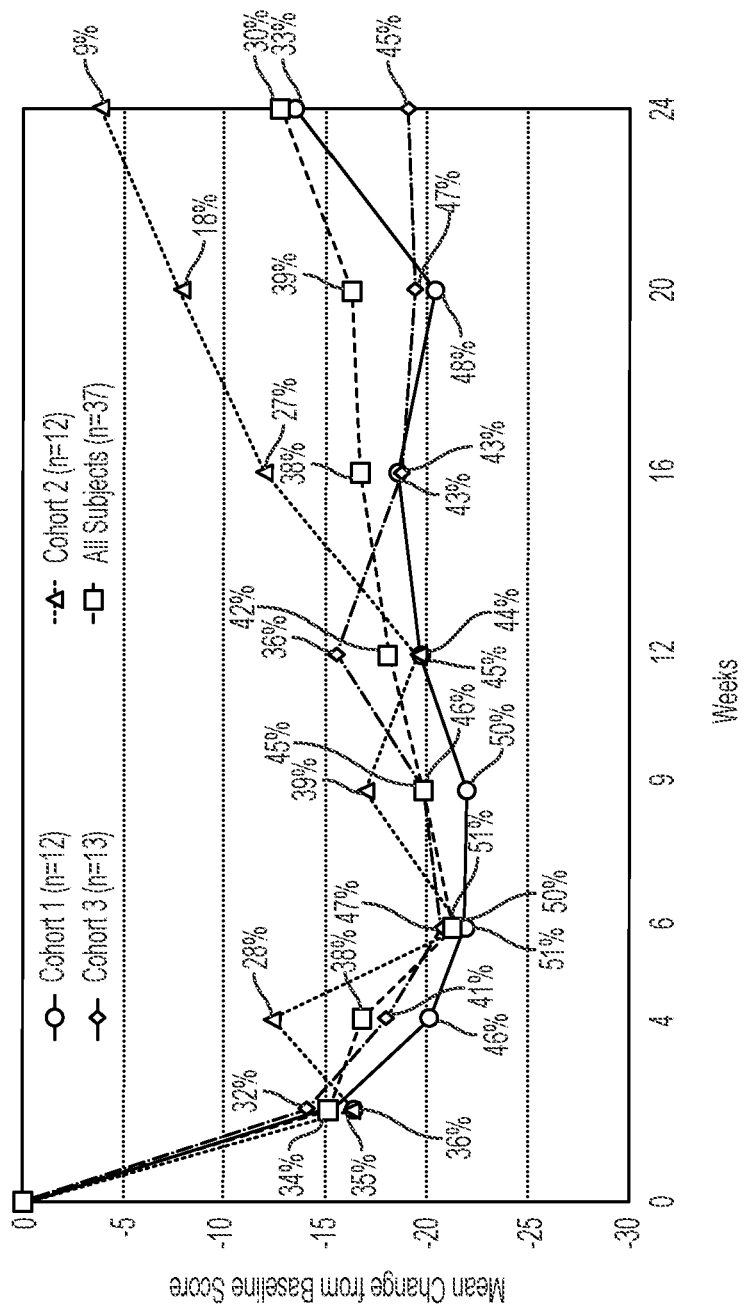
FIG. 5 shows Secondary Endpoint by Cohort—Change from Baseline in TWSTRS-Total Score over Time in the Study as described in the Example herein.
Figure 6:
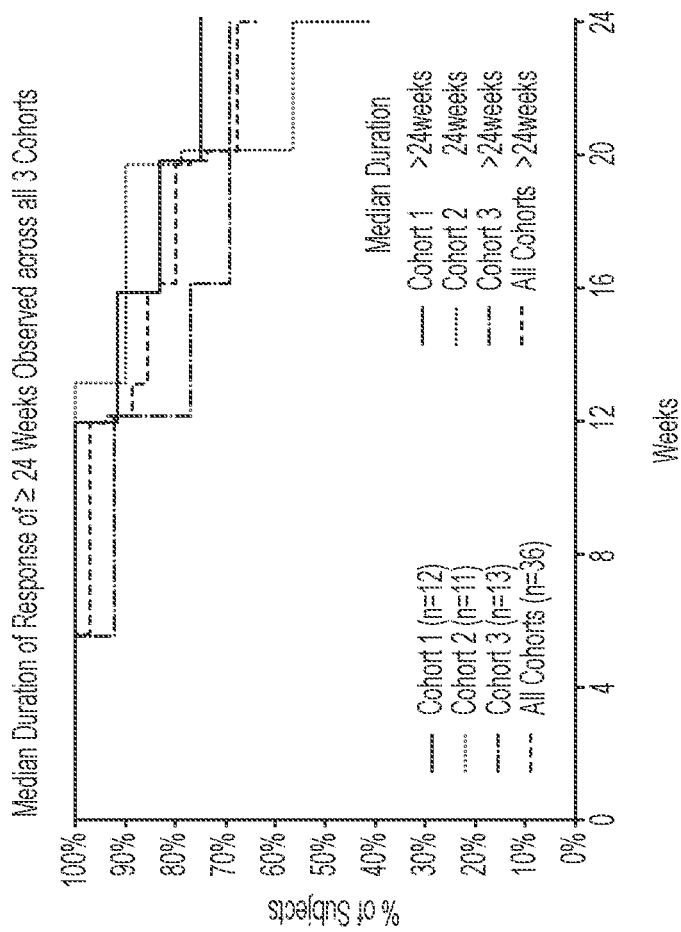
FIG. 6 shows Secondary Endpoint by Cohort—Duration of Response Defined by Subject Reaching Target-TWSTRS Score (of subjects with improvement at Week 4. Withdrawals due to need for retreatment are considered as events) in the Study as described in the Example herein.
Figure 7:
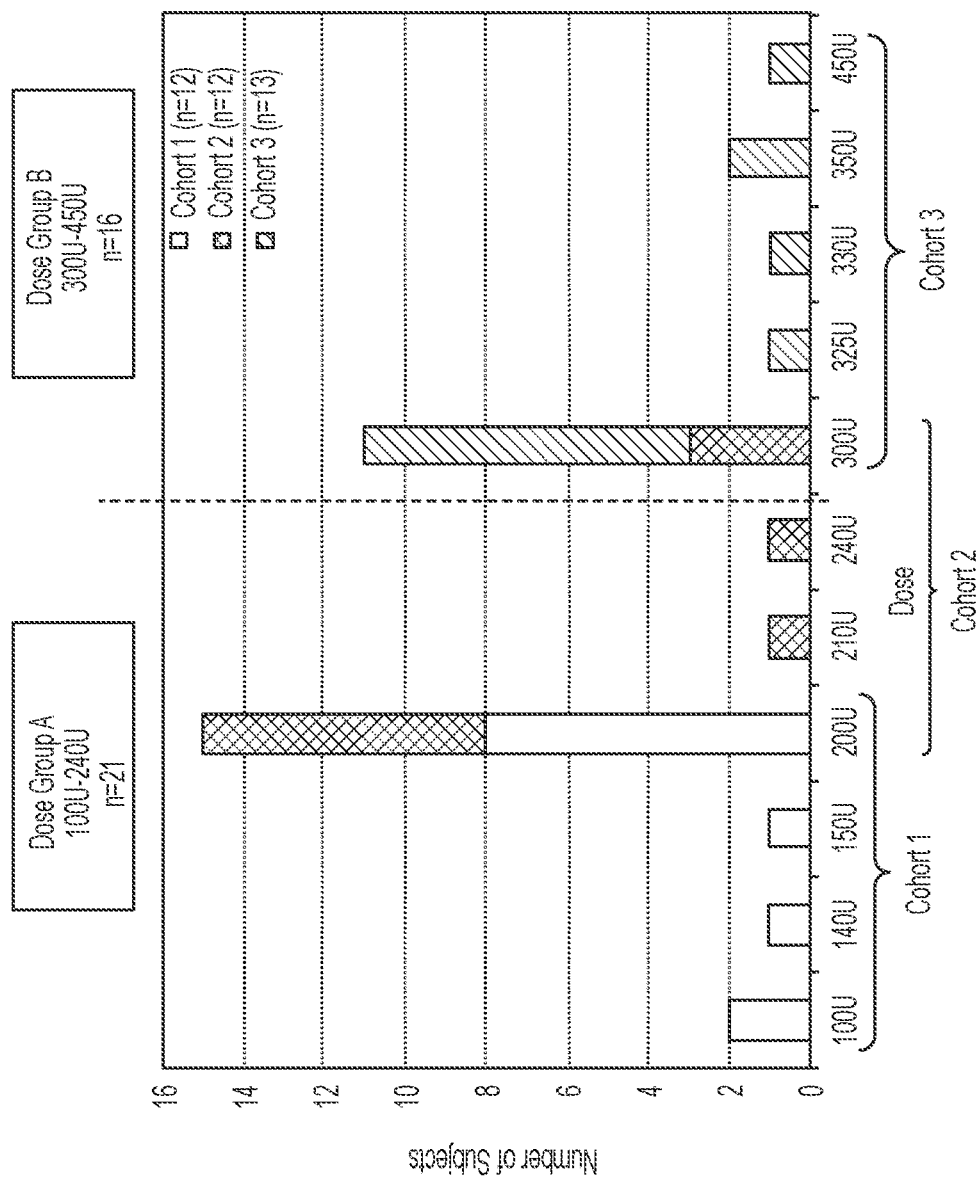
FIG. 7 shows Subject Distribution by Dose—Study Doses administered cluster into Two Separate Dose Groups in the Study as described in the Example herein.
Figure 8:
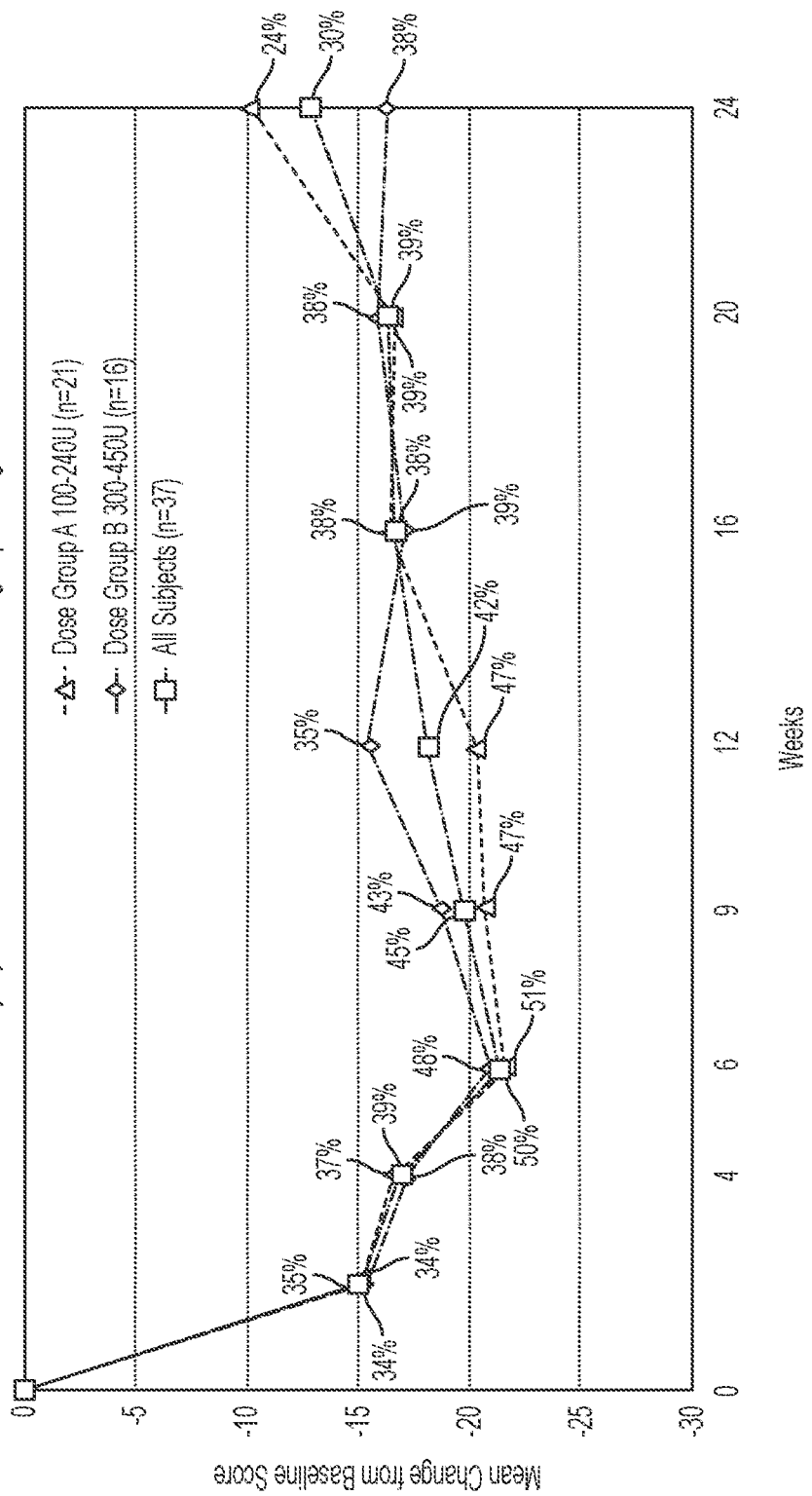
FIG. 8 shows Secondary Endpoint by Dose Group—Change from Baseline in TWSTRS-Total Score over Time as described in the Example herein.

Patients with cervical dystonia suffer from considerable pain and debilitation, which dramatically impacts their quality of life. Nearly all subjects in this study responded to treatment and a majority were still responding to RT002 at 24 weeks. FIGS. 1-8 provide additional data regarding the study design and results.

The Safety Summary of the study: RT002 appeared to be generally safe and well tolerated through Week 24 across all dose groups evaluated, with no increase in Treatment-Emergent Adverse Event's (TEAE's) upon dose escalation.

Total of 22 Treatment-Related TEAE's reported in 13 of 37 subjects (35%)
- Most frequently reported: dysphagia (14%), injection site erythema (8%), injection site bruising (5%), injection site pain (5%), muscle tightness (5%) and muscular weakness (5%)
- All TEAE's were mild or moderate in severity except for one case of neck pain reported as severe (Day 10 onset, duration of 2 days)
- No Serious Adverse Events were reported.
- All treatment-related TEAE's of special interest resolved with similar or lower incidence rates vs. prior BoNTA studies (Trials of other BoNTA products approved to treat CD have dysphagia rates ranging from 13-39%; Includes BOTOX, Dysport and Xeomin. Data as reported in product prescribing information).
  - Dysphagia: 14% (5/37; all mild); average duration 35 days.
  - Muscular Weakness: 5% (2/37; 1 mild, 1 moderate), both local
  - Neck pain: 3% (1/37; severe)

The Efficacy Summary of the Study:
- Duration of Effect: The median duration of effect, defined as subjects maintaining at least 20% of the treatment benefit achieved at Week 4 (Target TWSTRS Score), was >24 Weeks for each of the 3 cohorts studied
- When analyzed by Dose Groups A and B, the median duration of effect was >24 weeks for both groups
- Improvement in CD Signs and Symptoms: A clinically significant reduction from baseline in the TWSTRS Total Score of 38% was observed at Week 4 across all subjects
- The improvement from baseline peaked at 50% at Week 6, with the majority of this treatment benefit maintained at >30% through Week 24
- Global Impression of Change Response Rate: 97% of all subjects experienced improvement (Score >1) at Week 4 in their cervical dystonia symptoms as assessed by Clinician Global Impression of Change (CGIC)

In a preferred embodiment of this invention the injectable composition of the invention containing botulinum toxin A and a positively charged carrier comprising a positively charged polylysine polypeptide having covalently attached one or more positively charged efficiency groups, called RT002. The RT002 product is an injectable formulation, which contains the 150 kD subtype A botulinum toxin molecule, which is not covalently associated with a positively charged carrier peptide having the formula RKKRRQRRRG-(K)$_{15}$-GRKKRRQRRR (SEQ ID NO: 4), and which does not contain accessory proteins or animal-derived components. of the preferred method of this invention a single (one-time) treatment by injection of RT002 for the treatment of cervical dystonia is administered, optionally at different muscle locations on a subjects neck. The preferred treatment dose is more than 100 U, 100-200 U, 200-300 U and 300-450 U, of RT002 The RT002 product is composed of purified 150 kDa botulinum neurotoxin, referred to as RTT150, formulated in a lyophilized powder. In nonclinical studies, RT002 has been shown to exhibit less diffusion than other forms of botulinum neurotoxin A (BoNTA) and may offer more control of effect at target sites with less side effects due to distant spread of toxin into neighboring muscles. In addition, the RT002 additive-free botulinum toxin type A formulation has the ability to afford less immunogenic potential due to the absence of non-active proteins present in the formulation. In addition, RT002 was well tolerated after repeat dose intramuscular administration of up to 50 U/kg in rats.

Dosing regimen and injection technique: The preferred dosing regimen of RT002 of this invention is a single treatment of RT002 (dosed at up to 100 U, 100-200 U, 200-300 U or 300-450 U per subject, as a 0.1 mL intramuscular injection into injections sites on the neck of the subject undergoing treatment.

The reduced diffusion of RT002 is consistent with nonclinical and prior studies and supports a reduced spread of toxin, as observed in subjects treated with compositions of the invention which contain botulinum toxin, such as botulinum toxin A, and a positively charged carrier comprising a backbone, such as polylysine, with one or more covalently attached, positively charged efficiency groups as described herein, such as RT002.

Dosage and Duration of Effect: Without wishing to be limiting, the interim analysis results support a dose selection of more than 100 U as an optimal dose for single treatment with the botulinum containing compositions of the invention, based on the high responder rates, duration of effect and positive safety profile. In addition, the compositions of the invention, such as RT002, have a sustained and long lasting duration of effect, e.g., for at least 6 months, following administration by injection to a subject. The duration of effect provided by compositions of the invention, such as RT002, as well as treatment methods and uses thereof afford advantages in that subjects undergoing treatment consider that duration of effect following treatment is of high importance to them. Such a long, sustained duration of effect, particularly achieved by a single or one-time injection dose of product, namely, RT002, permits fewer injections per treatment course for a subject, which is important for the subject's comfort, convenience and overall well-being. A product that affords significant and sustained effects, which are maintained for at least a 6-month period following a single treatment dose by injection of the product to a subject provides a solution to an unmet need in the art for both practitioners and patients.

It is understood that the following examples and embodiments described herein are for illustrative purposes and that various modifications or changes in light thereof will be suggested to persons skilled in the art and are to be included within the spirit and purview of this application and scope of the appended claims.

All publications, patents, and published patent applications cited herein are hereby incorporated by reference in their entireties for all purposes.

The invention claimed is:

1. A method of treating cervical dystonia in an individual in need of treatment, the method comprising:
   administering by a plurality of injections a first treatment dose of a sterile injectable composition into a plurality of the muscles in the affected area in the individual in need of treatment to achieve a therapeutic effect following the first treatment;
   wherein the composition comprises a pharmaceutically acceptable diluent suitable for injection;
   a botulinum toxin component is botulinum toxin of serotype A having a molecular weight of 150 kDa; and
   a positively charged carrier component having the amino acid sequence RKKRRQRRRG-(K)15-GRKKRRQRRR (SEQ ID NO: 4);
   wherein the total first treatment dose of botulinum toxin component administered to the individual is 100 U to 300 U;
   wherein the positively charged carrier is non-covalently associated with the botulinum toxin component; and
   wherein the first treatment of the composition administered by the plurality of injections to the individual achieves a therapeutic effect of at least about 24 weeks, before a second or subsequent treatment with botulinum toxin is administered.

2. A method of treating cervical dystonia in an individual in need thereof, the method comprising:
   administering to the individual by a plurality of injections to a plurality muscles causing the cervical dystonia in the individual,
   a composition comprising:
      a pharmaceutically acceptable diluent for injection;
      a botulinum toxin component is botulinum toxin of serotype A having a molecular weight of 150 kDa; and
   a positively charged carrier component having the amino acid sequence RKKRRQRRRG-(K)15-GRKKRRQRRR (SEQ ID NO: 4);
      wherein the botulinum toxin is administered to the individual in a total treatment dose amount of 100 U to 300 U;
      wherein the positively charged carrier is non-covalently associated with the botulinum component; and
      wherein the plurality of injections of the composition provides a single treatment dose having at least about a 24 week duration of effect in reducing the symptoms of cervical dystonia in the individual, thereby extending treatment interval duration for the individual.

3. The method according to claim 2, wherein the composition achieves the extended duration therapeutic effect for at least about 8 months.

4. The method according to claim 2 wherein the composition does not locally diffuse from the site of injection following injection.

5. The method according to claim 2, wherein the treatment dose of botulinum toxin is administered to the individual in an amount of about 100 U to 200 U.

6. The method according to claim 2, wherein the treatment dose of botulinum toxin is administered to the individual in an amount of about 200 U to 300 U.

7. The method according to claim 2, wherein the duration of treatment effect comprises at least 6 months through 10 months.

8. A method of treating cervical dystonia in an individual in need of treatment, wherein the method of treatment comprises a treatment course having multiple treatment intervals, the treatment course comprising:
   administering by a plurality of injections an initial treatment dose of a sterile injectable composition into a plurality of muscles causing cervical dystonia in the individual to achieve a therapeutic effect of reducing the symptoms of cervical dystonia following the initial treatment with the composition;
      wherein the composition comprises a pharmaceutically acceptable diluent suitable for injection;
   a botulinum toxin component is botulinum toxin of serotype A having a molecular weight of 150 kDa; and
   a positively charged carrier component; and
   wherein the botulinum toxin component is administered to the individual in a treatment dose of about 100 U to about 300 U;
   wherein the positively charged carrier is non-covalently associated with the botulinum toxin component;
   wherein the initial treatment dose of the composition administered by the plurality of injections to the individual provides a therapeutic duration of effect lasting through at least about 10 months; and
   administering at least one subsequent treatment dose of the composition by a plurality of injections to the individual at a treatment interval comprising a duration of greater than or equal to 6 months to at least about 10 months following the initial treatment dose and between each subsequent treatment dose.

9. The method according to claim 2, wherein the one or more muscles receiving an injection consist of sternocleidomastoideoator scapulae, scalenus complex, splenius capitis, splenius cervices, trapezius, and longissimus.

\* \* \* \* \*